US008483838B2

(12) United States Patent
Nghiem et al.

(10) Patent No.: US 8,483,838 B2
(45) Date of Patent: *Jul. 9, 2013

(54) ANTENNA ARRANGEMENTS FOR IMPLANTABLE THERAPY DEVICE

(75) Inventors: David Nghiem, Shoreview, MN (US); Scott Anthony Lambert, East Bethel, MN (US); Jason William Sprain, Shoreview, MN (US)

(73) Assignee: EnteroMedics Inc., St. Paul, MN (US)

( * ) Notice: Subject to any disclaimer, the term of this patent is extended or adjusted under 35 U.S.C. 154(b) by 221 days.

This patent is subject to a terminal disclaimer.

(21) Appl. No.: 13/036,614

(22) Filed: Feb. 28, 2011

(65) Prior Publication Data
US 2011/0152971 A1    Jun. 23, 2011

Related U.S. Application Data

(63) Continuation of application No. 12/108,225, filed on Apr. 23, 2008, now Pat. No. 7,917,226.

(51) Int. Cl.
*A61N 1/00* (2006.01)
(52) U.S. Cl.
USPC .............................. 607/60; 607/36
(58) Field of Classification Search
USPC .......................... 607/30, 32, 36, 60
See application file for complete search history.

(56) References Cited

U.S. PATENT DOCUMENTS

| | | |
|---|---|---|
| 3,942,535 A | 3/1976 | Schulman |
| 4,041,955 A | 8/1977 | Kelly et al. |
| 4,071,032 A | 1/1978 | Schulman |
| 4,142,533 A | 3/1979 | Brownlee et al. |
| 4,332,256 A | 6/1982 | Brownlee et al. |
| 4,441,498 A | 4/1984 | Nordling |
| 4,542,532 A | 9/1985 | McQuilkin |
| 4,562,841 A | 1/1986 | Brockway et al. |
| 4,681,111 A | 7/1987 | Silvian |
| 5,314,457 A | 5/1994 | Jeutter et al. |
| 5,342,408 A | 8/1994 | deCoriolis et al. |
| 5,683,432 A | 11/1997 | Goedeke et al. |
| 5,697,958 A | 12/1997 | Paul et al. |
| 5,713,939 A | 2/1998 | Nedungadi et al. |
| 5,861,019 A | 1/1999 | Sun et al. |
| 6,009,350 A | 12/1999 | Renken |
| 6,009,878 A | 1/2000 | Weijand et al. |
| 6,169,925 B1 | 1/2001 | Villaseca et al. |
| 6,240,317 B1 | 5/2001 | Villaseca et al. |

(Continued)

FOREIGN PATENT DOCUMENTS
WO    WO 00/08712    2/2000

OTHER PUBLICATIONS

Invitation to Pay Additional Fees with Partial International Search mailed Mar. 19, 2010.

(Continued)

*Primary Examiner* — Brian T Gedeon
(74) *Attorney, Agent, or Firm* — Merchant & Gould, P.C.

(57) ABSTRACT

Embodiments of an implantable medical device includes a loop antenna wound about an inner housing. The loop antenna may form a partial winding, a complete winding, or multiple windings about the inner housing. One or more additional antennae may be capacitively coupled to the loop antenna external to the inner housing to increase efficiency and decrease Return Loss Response of the implantable device. The additional antenna may be balanced or unbalanced antennae.

20 Claims, 24 Drawing Sheets

U.S. PATENT DOCUMENTS

| | | |
|---|---|---|
| 6,342,408 B1 | 1/2002 | Oowaki et al. |
| 6,379,300 B1 | 4/2002 | Haubrich |
| 6,381,496 B1 | 4/2002 | Meadows et al. |
| 6,388,626 B1 | 5/2002 | Gamalielsson et al. |
| 6,434,429 B1 | 8/2002 | Kraus et al. |
| 6,456,256 B1 | 9/2002 | Amundson et al. |
| 6,456,883 B1 | 9/2002 | Torgerson et al. |
| 6,470,215 B1 | 10/2002 | Kraus et al. |
| 6,490,487 B1 | 12/2002 | Kraus et al. |
| 6,505,072 B1 | 1/2003 | Linder et al. |
| 6,574,509 B1 | 6/2003 | Kraus et al. |
| 6,614,406 B2 | 9/2003 | Amundson et al. |
| 6,622,043 B1 | 9/2003 | Kraus et al. |
| 6,708,065 B2 | 3/2004 | Von Arx et al. |
| 6,763,269 B2 | 7/2004 | Cox |
| 6,804,559 B1 | 10/2004 | Kraus et al. |
| 6,809,701 B2 | 10/2004 | Amundson et al. |
| 6,893,395 B1 | 5/2005 | Kraus et al. |
| 6,993,393 B2 | 1/2006 | Von Arx et al. |
| 7,016,733 B2 | 3/2006 | Dublin et al. |
| 7,047,076 B1 | 5/2006 | Li et al. |
| 7,110,823 B2 | 9/2006 | Whitehurst et al. |
| 7,123,206 B2 | 10/2006 | Hess et al. |
| 7,164,950 B2 | 1/2007 | Kroll et al. |
| 7,177,700 B1 | 2/2007 | Cox |
| 7,211,048 B1 | 5/2007 | Najafi et al. |
| 7,225,029 B2 | 5/2007 | Shankar et al. |
| 7,281,314 B2 | 10/2007 | Hess et al. |
| 7,289,855 B2 | 10/2007 | Nghiem et al. |
| 7,299,086 B2 | 11/2007 | McCabe et al. |
| 7,467,014 B2 | 12/2008 | Fuller et al. |
| 2002/0123776 A1 | 9/2002 | Von Arx et al. |
| 2003/0025645 A1 | 2/2003 | Amundson et al. |
| 2003/0083719 A1 | 5/2003 | Shankar et al. |
| 2003/0088295 A1 | 5/2003 | Cox |
| 2003/0114897 A1 | 6/2003 | Von Arx et al. |
| 2003/0114898 A1 | 6/2003 | Von Arx et al. |
| 2003/0229383 A1 | 12/2003 | Whitehurst et al. |
| 2004/0015199 A1 | 1/2004 | Thompson et al. |
| 2004/0027306 A1 | 2/2004 | Amundson et al. |
| 2004/0088012 A1 | 5/2004 | Kroll et al. |
| 2004/0176811 A1 | 9/2004 | Von Arx et al. |
| 2004/0215280 A1 | 10/2004 | Dublin et al. |
| 2005/0075693 A1 | 4/2005 | Toy et al. |
| 2005/0088357 A1 | 4/2005 | Hess et al. |
| 2005/0113886 A1 | 5/2005 | Fischell et al. |
| 2005/0134520 A1 | 6/2005 | Rawat et al. |
| 2005/0137480 A1 | 6/2005 | Alt et al. |
| 2005/0197674 A1 | 9/2005 | McCabe et al. |
| 2005/0203583 A1 | 9/2005 | Twetan et al. |
| 2005/0203584 A1 | 9/2005 | Twetan et al. |
| 2005/0288600 A1 | 12/2005 | Zhang et al. |
| 2006/0069322 A1 | 3/2006 | Zhang et al. |
| 2006/0100670 A1 | 5/2006 | Sweeney |
| 2006/0116593 A1 | 6/2006 | Zhang et al. |
| 2006/0116744 A1 | 6/2006 | Von Arx et al. |
| 2006/0142820 A1 | 6/2006 | Von Arx et al. |
| 2006/0206170 A1 | 9/2006 | Denker et al. |
| 2006/0224206 A1 | 10/2006 | Dublin et al. |
| 2006/0224207 A1 | 10/2006 | Dublin et al. |
| 2006/0227060 A1 | 10/2006 | Hess et al. |
| 2006/0241724 A1 | 10/2006 | Dublin et al. |
| 2006/0247711 A1 | 11/2006 | Verhoef et al. |
| 2006/0247712 A1 | 11/2006 | Fuller et al. |
| 2006/0253043 A1 | 11/2006 | Zhang et al. |
| 2006/0253044 A1 | 11/2006 | Zhang et al. |
| 2006/0253162 A1 | 11/2006 | Zhang et al. |
| 2006/0253164 A1 | 11/2006 | Zhang et al. |
| 2006/0293607 A1 | 12/2006 | Alt et al. |
| 2007/0027505 A1 | 2/2007 | Ginggen |
| 2007/0060967 A1 | 3/2007 | Strother et al. |
| 2007/0100377 A1 | 5/2007 | Armstrong et al. |
| 2007/0100384 A1 | 5/2007 | Fischell et al. |
| 2007/0100385 A1 | 5/2007 | Rawat et al. |
| 2007/0123949 A1 | 5/2007 | Dabney et al. |
| 2007/0135882 A1 | 6/2007 | Drasler et al. |
| 2007/0135883 A1 | 6/2007 | Drasler et al. |
| 2007/0150009 A1 | 6/2007 | Kveen et al. |
| 2007/0191910 A1 | 8/2007 | Ren |
| 2007/0225596 A1 | 9/2007 | Iustin et al. |
| 2007/0288066 A1 | 12/2007 | Christman et al. |
| 2008/0021522 A1 | 1/2008 | Verhoef et al. |
| 2008/0039898 A1 | 2/2008 | Lim et al. |
| 2009/0248112 A1* | 10/2009 | Mumbru et al. ............ 607/60 |

OTHER PUBLICATIONS

International Search Report and Written Opinion mailed Jun. 9, 2010.

* cited by examiner

ANTENNA ARRANGEMENTS FOR IMPLANTABLE THERAPY DEVICE

CROSS REFERENCE TO RELATED APPLICATION

This application is a continuation of application Ser. No. 12/108,225, now U.S. Pat. No. 7,917,226, filed Apr. 23, 2008, which application is incorporated herein by reference in its entirety.

BACKGROUND

Implantable medical devices, including neurological devices and cardiac rhythm management devices, such as pacemakers and implantable cardioverter/defibrillators, typically have the capability to communicate data and commands with a device called an external programmer via a radio-frequency telemetry link. A clinician may use such an external programmer to program the operating parameters of the implantable medical device. Furthermore, such characteristics may be modified after implantation in this manner. Additionally, some implantable medical devices, most notably neurological devices, contain rechargeable batteries, which are recharged via low frequency, near-field telemetry.

Modern implantable devices also include the capability for bidirectional communication so that information can be radiated to the external programmer from the implantable device. Among the data which may typically be telemetered to and from an implantable device are various operating parameters and physiological data, the latter either collected in real-time or stored from previous monitoring operations. Examples of commands telemetered to and from an implantable device may include instructions to begin or end treatment or instructions to utilize a particular treatment schedule or predetermined treatment program.

Telemetry systems for implantable medical devices may utilize radio-frequency energy to enable bidirectional communication between the implantable device and an external programmer.

SUMMARY

This invention pertains to implantable medical devices such as implantable neurostimulators, neuroblockers or neuromodulators. In particular, the invention relates to an apparatus and method for enabling radio-frequency telemetry in such devices.

According to aspects of the disclosure, an implantable medical device includes an antenna arrangement including a loop antenna wound about an inner housing.

According to other aspects of the disclosure, an implantable device includes an antenna arrangement including a loop antenna capacitively coupled to one or more additional antennae located external to the inner housing to increase antenna aperture of the additional antennae. The additional antennae may be balanced or unbalanced.

The methods, systems, and devices as described herein are applicable to a wide variety of therapies including cardiac pacing with electrodes applied to heart tissue, gastro-intestinal disorders such as obesity, pancreatitis, irritable bowel syndrome, inflammatory disorders, and diabetes. In an embodiments, methods, systems, and devices are provided for the treatment of a gastrointestinal disorder by the application of a high frequency signal to the vagus nerve of a patient.

Implantable therapy systems are disclosed herein for applying therapy to an internal anatomical feature of a patient.

DETAILED DESCRIPTION

The methods, devices and systems as described herein are applicable to treating a wide variety of medical conditions, such as cardiac arrhythmias or other cardio-pulmonary conditions, pancreatitis, diabetes, incontinence, gastro-esophageal reflux disease (GERD), or obesity or other gastro-intestinal disorders. The methods, devices and systems as described herein also may be applicable to pain management, tissue ablation systems, implantable drug pumps (e.g., insulin pumps), and implantable condition monitoring devices.

In embodiments, the disclosure provides an implantable medical device comprising: an inner housing containing a processor and a communications circuit; a first antenna arrangement wrapped circumferentially around the inner housing, the first antenna arrangement having a first port at which the first antenna arrangement enters the inner housing, the first antenna arrangement being electrically coupled to the communications circuit via the first port, the first antenna arrangement including a loop antenna that is electrically coupled to the communications circuit via the first port; and a second antenna arrangement arranged external of the inner housing, the second antenna arrangement having a second port at which the second antenna arrangement enters the inner housing, the second antenna arrangement being capacitively coupled to the loop antenna; wherein the implantable medical device is configured for implantation within a body of a patient.

Another aspect of the disclosure provides a method for communicating with an implantable device, the method comprising: providing an implantable device including a loop antenna wound around an exterior of an inner housing containing a processor, a communications circuit, a rechargeable power source, and a switching circuit, the implantable device also including a second antenna capacitively coupled to the loop antenna; implanting the implantable device within the patient; transmitting a power signal to the implantable device to provide power to the rechargeable power source, the power signal having a first frequency; and transmitting a communication signal to the implantable device to provide data or commands to the communications circuit. In one embodiment, the communications signal has a second frequency that is higher than the first frequency.

DEFINITIONS

As the term is used herein, an antenna arrangement includes an arrangement of one or more antennae. If the antenna arrangement includes multiple antennae, then each antenna in the arrangement may be capacitively coupled or decoupled from each of the other antennae.

Illustrated Embodiments

With reference now to the various drawing figures in which identical elements are numbered identically throughout, a description of the preferred embodiments of the present invention will now be described.

Figure 1:
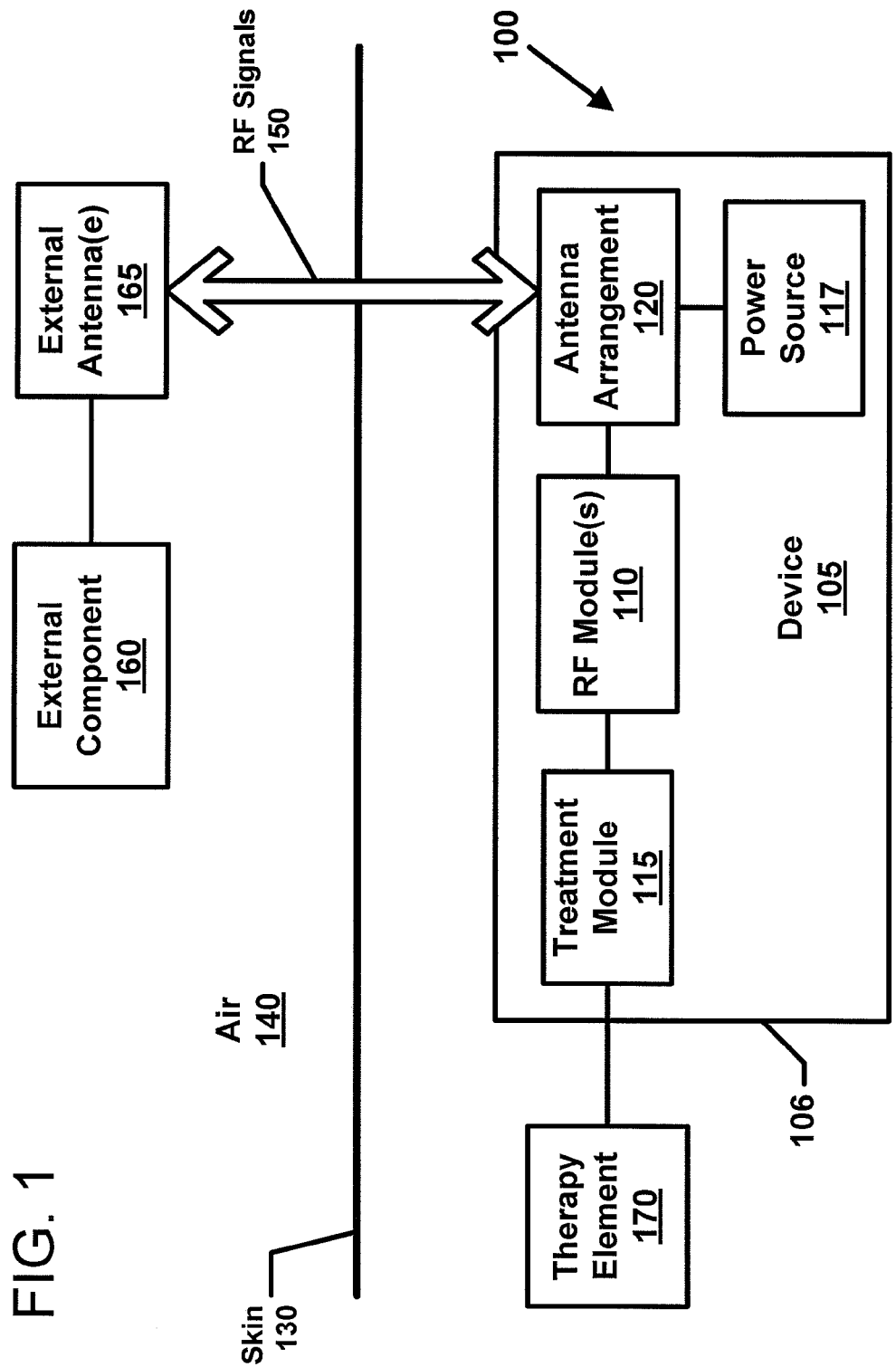
FIG. 1 is a schematic block diagram of an example therapy system for treating a medical condition, such as obesity, in accordance with the principles of the present disclosure as described herein.

FIG. 1 is a schematic block diagram of a therapy system 100 for treating a medical condition, such as obesity. The therapy system 100 includes a sealed implantable device 105, at least one therapy and/or diagnostic element 170, and an external component 160 configured to communicate with the implantable device 105 via an implantable antenna arrangement 120. The implantable device 105 and implantable antenna arrangement 120 are adapted for implantation beneath the skin layer 130 of a patient to be treated. In some embodiments, the implantable device is hermetically sealed.

In general, the implantable device 105 includes a housing 106 that provides a sealed enclosure in which circuitry of the implantable device may be housed. In the example shown in FIGS. 1 and 2, the housing 106 contains a communications circuit (e.g., an RF module) 110 and a treatment module 115. In one embodiment, the housing 106 provides electrical shielding for the RF module 110 and the treatment module 115. In another embodiment, the housing 106 may provide a grounding plane for one or more antennae of the antenna arrangement 120 coupled to the implantable device 105. For example, the housing 106 may be formed from one or more conductive materials (e.g., Titanium, Niobium, Platinum, Indium, stainless steel, MP35N alloys, or other biocompatible materials). In another embodiment, the housing 106 may be plated with a conductive material (e.g., Gold plated over Copper). In other embodiments, however, non-conductive layers may be added in or around all or part of the housing 106 as will be disclosed in greater detail herein.

In general, the treatment module 115 manages treatment of the patient. The treatment module 115 is configured to communicate with the therapy element and/or diagnostic element 170. In one embodiment, the treatment module 115 is configured to generate a therapy signal and to communicate (e.g., electrically) the therapy signal to the therapy element (e.g., lead electrodes) 170 to provide treatment to the patient. In another embodiment, the treatment module 115 obtains readings indicating a condition of the patient from a diagnostic device (e.g., a temperature sensor, an accelerometer, etc.).

The therapy element 170 provides electrical signals (e.g., pulses) to at least one area of the patient's body in accordance with the therapy signals generated by the treatment module 115. For example, the therapy element 170 may include two or more electrical lead assemblies (not shown) that couple to nerves, muscles, organs, or other tissue of the patient. In some embodiments, the electrical lead assembly comprises a lead and one or more electrodes. In one embodiment, the therapy and/or diagnostic element 170 is arranged external to the hermetically sealed implantable device 105. In another embodiment, the therapy and/or diagnostic element 170 is arranged within the hermetically sealed implantable device 105.

In one embodiment, the therapy element 170 up-regulates and/or down-regulates one or more nerves of a patient based on the therapy signals provided by the treatment module 115. For example, electrodes may be individually placed on the anterior vagus nerve and posterior vagus nerve, respectively, of a patient. In embodiments, the placement of the electrodes on the vagus nerve may vary. In an embodiment the electrode is placed below the innervation of the heart such as in sub diaphragmatic location. In other embodiments, however, fewer or greater electrodes can be placed on or near fewer or greater nerves. In still other embodiments, the therapy element 170 may provide electrical signals directly to the patient's organs, such as the heart, lungs, and/or stomach, or to the patient's muscles, such as the sphincter muscle, or to other tissue of the patient.

The external component 160 includes circuitry for communicating with the implantable device 105. In general, communication is transmitted through the skin 130 of the patient along a two-way signal path as indicated by double-headed arrow 150. Example communication signals include power signals, data signals, and command signals. In general, the RF module 110 controls when power signals, data signals, and/or command signals are radiated to and from the implantable device 105 within the near-field and/or the far-field.

In the example shown, the external component 160 can communicate with the implantable device 105 via bidirectional telemetry (e.g. via radiofrequency (RF) signals). In one embodiment, the external component 160 may provide power to the implantable device 105 via an RF link. In another embodiment, treatment instructions include treatment parameters, signal parameters, implantable device settings, treatment schedule, patient data, command signals, or other such signals may be communicated between the external component 160 and the implantable device 105.

The external component 160 shown in FIG. 1 includes another antenna arrangement 165 that can send and receive RF signals. The implantable antenna arrangement 120 may be implanted within the patient and coupled to the RF module 110 of the implantable device 105. In one embodiment, the implantable antenna arrangement 120 is integral with the implantable device 105. The implantable antenna arrangement 120 serves to radiate (e.g., receive and transmit) signals from and to the antenna arrangement 165 of the external component 160 within the near-field and/or the far-field. In one embodiment, the RF module 110 includes a matching circuit that optimizes the impedance of the antenna arrangement 120 for a particular frequency.

In some embodiments, the external component 160 and the RF module 110 can encode and decode information signals as bit streams by amplitude modulating, frequency modulating, or rectifying an RF carrier wave. In one embodiment, the signals radiated between the antenna arrangements 165, 120 have a carrier frequency of about 6.78 MHz. In other embodiments, however, higher or lower carrier wave frequencies and/or rectification levels may be used and other modulation methods and levels may be used.

In one embodiment, the implantable device 105 communicates with the external component 160 using load shifting. For example, load shifting can be achieved by modification of the load induced on the external component 160. This change in the load can be sensed by the inductively coupled external component 160. In other embodiments, however, the implantable device 105 and external component 160 can communicate using other types of signals.

In some embodiments, the RF module 110 of the implantable device 105 receives power from the external component 160. In some embodiments, the RF module 110 distributes the power to the treatment module 115 to generate the therapy signals. In one such embodiment, the treatment module 115 may depend entirely upon power received from an external source (e.g., the external component 160 or another external power source). In another embodiment, an implantable power source 117, such as a rechargeable battery, supplies the power to generate the therapy signals. In such an embodiment, the RF module 110 may distribute the power received from the external component 160 to the implantable power source 117 for recharging.

In some embodiments, the treatment module 115 initiates the generation and transmission of therapy signals to the therapy elements 170. In an embodiment, the treatment module 115 initiates therapy when powered by the implantable power source 117. In other embodiments, however, the external component 160 triggers the treatment module 115 to begin generating therapy signals. After receiving initiation signals from the external component 160, the treatment module 115 generates the therapy signals and transmits the therapy signals to the therapy elements 170.

In other embodiments, the external component 160 also can provide the instructions according to which the therapy signals are generated. Example parameters of therapy signals may include pulse-width, amplitude, frequency, ramping, duty cycle, treatment schedule, and other such parameters. In a preferred embodiment, the external component 160 includes memory in which several predetermined programs/ therapy schedules can be stored for transmission to the implantable device 105. The external component 160 also can enable a user to select a program/therapy schedule stored in memory for transmission to the implantable device 105. In another embodiment, the external component 160 can provide treatment instructions with each initiation signal.

Typically, each of the programs/therapy schedules stored on the external component 160 can be adjusted by a physician to suit the individual needs of the patient. For example, a computing device (e.g., a notebook computer, a personal computer, etc.) (not shown) can be communicatively connected to the external component 160. With such a connection established, a physician can use the computing device to program therapies into the external component 160 for either storage or transmission to the implantable device 105.

The implantable device 105 also may include memory (not shown) in which treatment instructions and/or patient data can be stored. For example, the implantable device 105 can store therapy programs indicating what therapy should be delivered to the patient. The implantable device 105 also can store patient data indicating how the patient utilized the therapy system 100 and/or reacted to the delivered therapy.

In a specific embodiment, as described below, the implantable device 105 contains a rechargeable battery from which the implantable device 105 may draw power.

Figure 2:
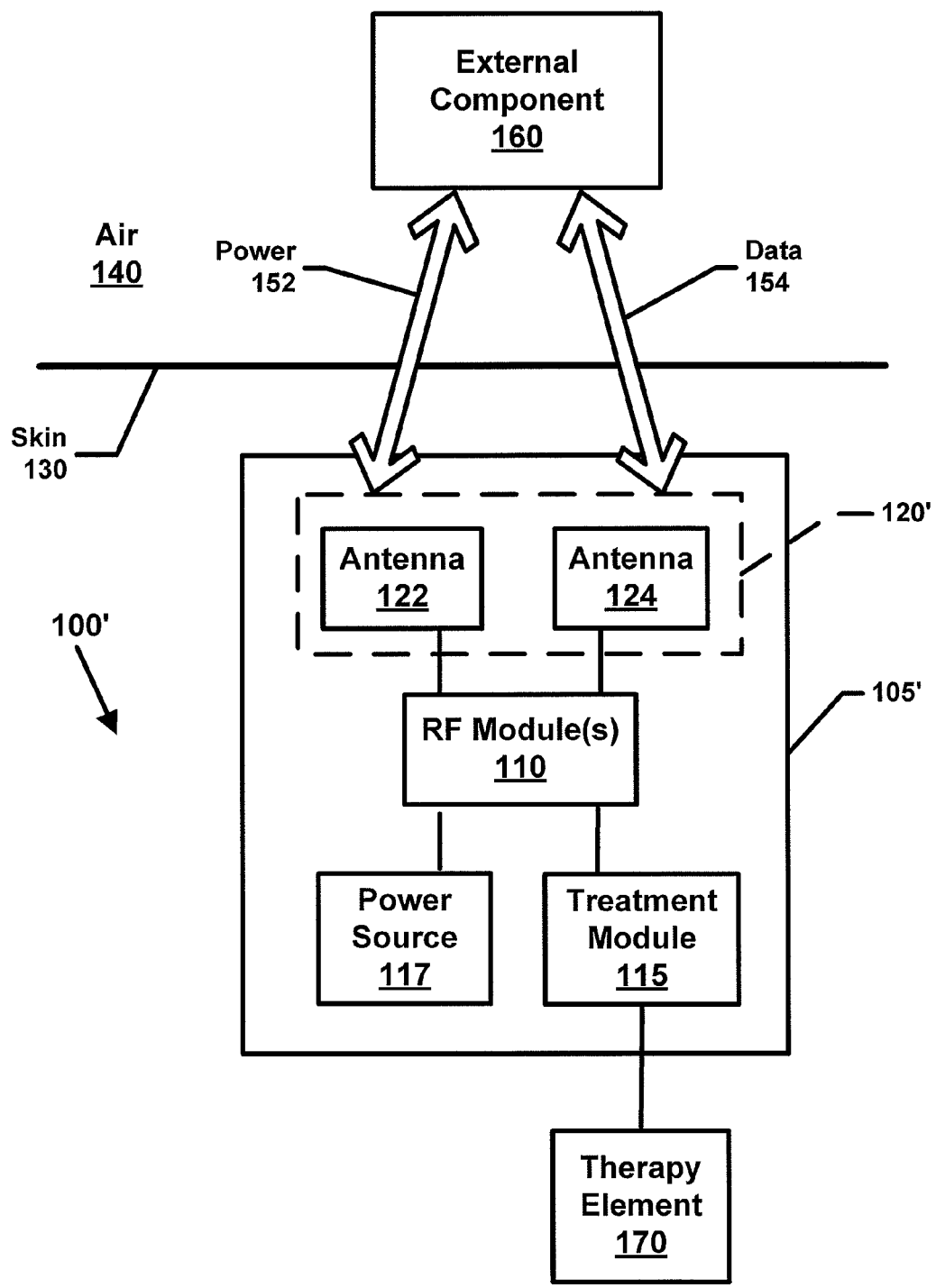
FIG. 2 is a schematic block diagram of another example therapy system including an implantable device, an external component, and a therapy element in accordance with the principles of the present disclosure as described herein.

FIG. 2 is a schematic block diagram of another therapy system 100' including an implantable device 105', an external component 160, and a therapy element 170. The implantable device 105' includes at least one RF module 110, a treatment module 115, and an antenna arrangement 120' including a first antenna arrangement 122 and a second antenna arrangement 124. In general, the first antenna arrangement 122 includes a loop antenna.

In one embodiment, the second antenna arrangement 124 includes an unbalanced antenna including, for example, an inverted-L antenna, a zigzag antenna, a helical antenna, a spiral antenna, a folded antenna, a serpentine antenna, or any other suitable antenna that is capacitively coupled to the first antenna arrangement 122. In another embodiment, the second antenna arrangement 124 includes a loop antenna that is capacitively coupled to the first antenna arrangement 122. In other embodiments, one or more antennae of the second antenna arrangement 124 may be decoupled from the antennae of the first antenna arrangement 122.

In some embodiments, the first antenna arrangement 122 receives power (see arrow 152) with which to operate the implantable device 105' and/or to recharge the power source 117. The second antenna arrangement 124 receives and transmits communication signals containing information (e.g., therapy parameters, schedules, patient data, etc.) and/or command signals (see arrow 154) from and to the external component 160. Advantageously, separating the functions of the antenna arrangements 122, 124 may allow for concurrent radiation of power and communication signals (e.g., commands and/or data). Separating the functions also may enable tuning each antenna arrangement 122, 124 to better implement a particular function, such as communication range or charging efficiency. In one embodiment, the first antenna arrangement 122 also can receive and transmit information signals from and to the external component 160.

Figure 24:
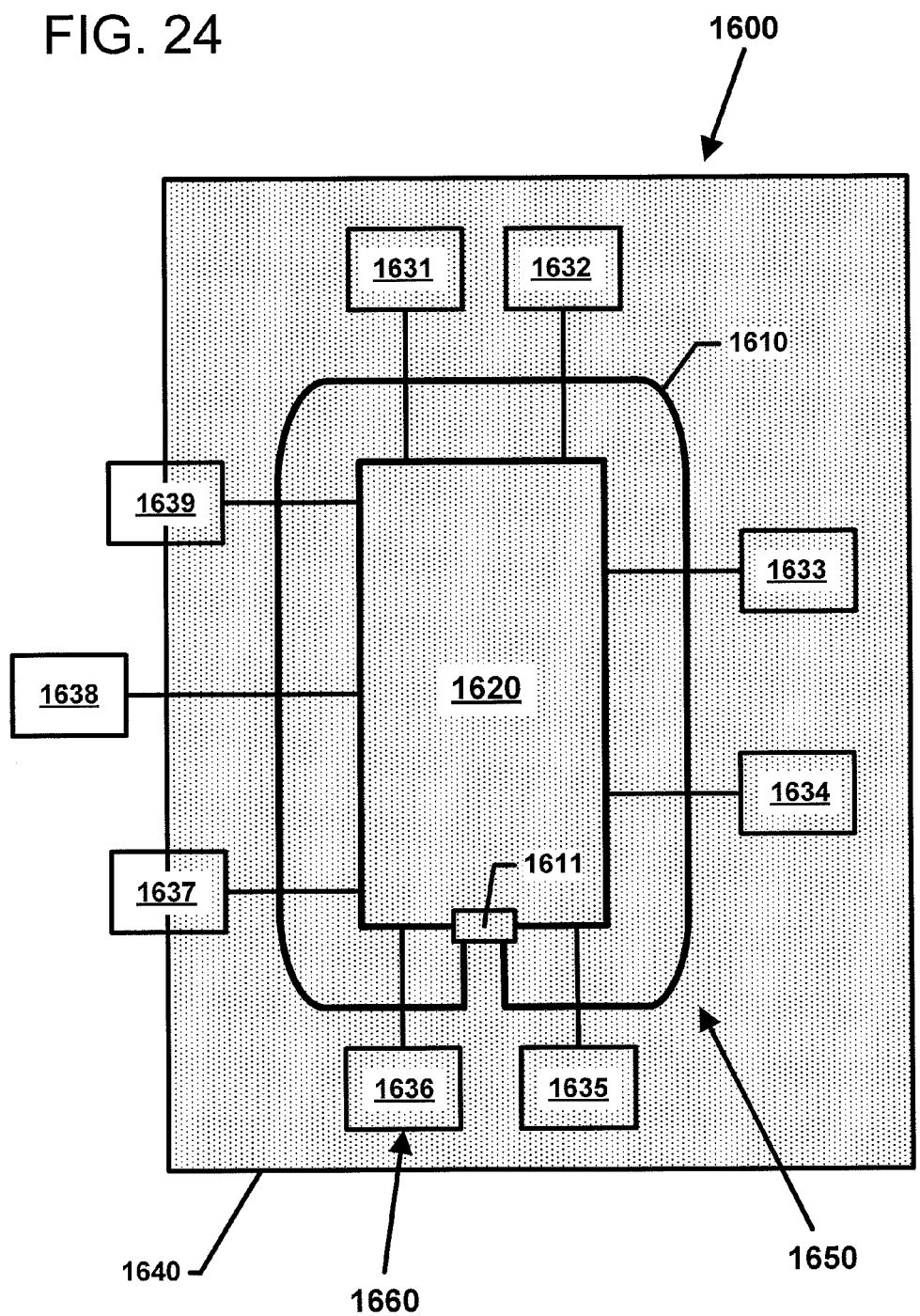
FIG. 24 is a schematic block diagram of an implantable device having an antenna arrangement including an array of antennae capacitively coupled to a loop antenna, the antenna arrangement being coupled to an inner housing in accordance with the principles of the present disclosure as described herein.

In other embodiments, the second antenna arrangement 124 may include an array of antennae (e.g., see FIG. 24). Each of the antennae in the antennae array may be capacitively coupled or decoupled to or from the first antenna arrangement 122 and/or each other antenna in the antennae array. As will be described in greater detail herein, the antennae of the array may be utilized to modify the direction, polarization, and/or gain of the information signals received and transmitted by the first antenna 122. Providing diversified antennae within the implantable device 105' also may enable tailoring of the RF signal to accommodate the location and/or orientation of the implantable device 105' with respect to an external source. Additional antennae also may be utilized to locate the implantable device 105' with respect to an external object, such as the external component 160.

Antenna Arrangements

The systems and devices as described herein comprise one or more antenna arrangements. The antenna arrangements facilitate communication and power signals as described herein. In embodiments, an implantable device comprises a first antenna arrangement wrapped circumferentially around the inner housing, the first antenna arrangement having a first port at which the first antenna arrangement enters the inner housing, the first antenna arrangement being electrically coupled to the communications circuit via the first port, the first antenna arrangement including a loop antenna that is electrically coupled to the communications circuit via the first port. The implantable device also may comprise a second antenna arrangement arranged external of the inner housing, the second antenna arrangement having a second port at which the second antenna arrangement enters the inner housing, the second antenna arrangement being capacitively coupled to the loop antenna. In some embodiments, the first and second antenna arrangements transmit at different frequencies.

Referring to FIGS. 3-12, different antenna arrangements and configurations may be utilized in the implantable devices disclosed herein, e.g., as implantable antenna arrangement 120. In FIGS. 3-12, the radiation capabilities of different types of antenna arrangements are shown relative to one another. In particular, five different types of antenna arrangements are presented and a numerically simulated Return Loss Response for each in free space is shown. The antenna arrangements in FIGS. 3-12 are not coupled to implantable devices. Rather, the numerical simulations are provided for the antenna arrangements positioned in free space in order to compare the radiation capabilities of the different antenna arrangements.

Return Loss Response (dB) is defined as a ratio of reflected signal power over input signal power. The Simulated Return Loss Response for each antenna arrangement provides information about the resonant frequencies, transmission range, radiation efficiency, and the number of resonant frequencies of the antenna arrangement. For example, dips in the Simulated Return Loss Response generally correspond with resonant frequencies of the antenna arrangement. Furthermore, the amplitude of the dips in the Simulated Return Loss Response generally corresponds with the efficiency (and hence power) of the antenna arrangement.

The Simulated Return Loss Response provides for a selection of different antenna arrangements depending on the requirements for a particular therapy system. For example, in some embodiments, it is desirable to transmit a power signal and a communication signal concurrently. In other embodiments, it may be desirable to eliminate a matching circuit in the device. In other embodiments, it may be desirable to eliminate resonant frequencies from an antenna arrangement.

Figure 3:
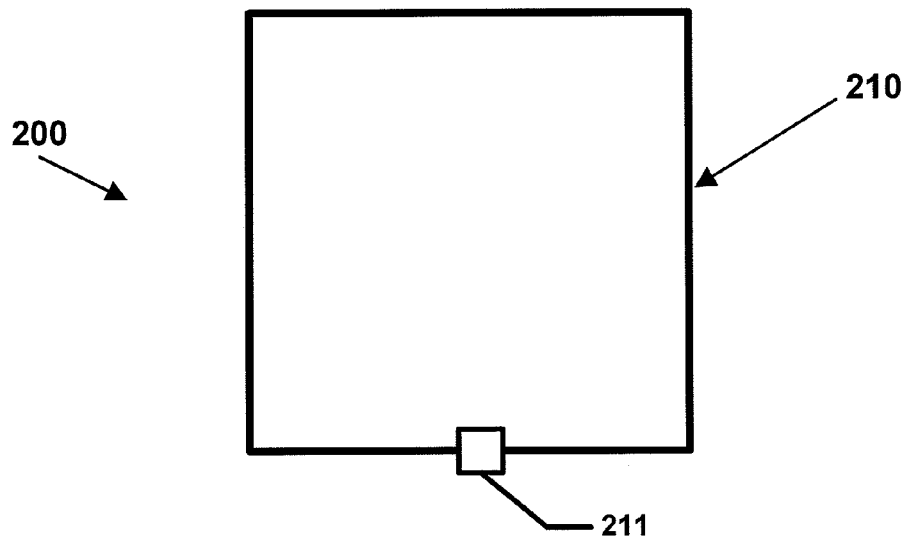
FIG. 3 is a schematic block diagram of one example antennae arrangement including an unloaded loop antenna that provides a control against which the Return Loss Response of other antennae configurations may be compared in accordance with the principles of the present disclosure as described herein.

For example, FIG. 3 is a schematic block diagram of a first example antenna arrangement 200 that may be used in the implantable devices disclosed herein. The antenna arrangement 200 includes a loop antenna 210 having a first port 211. In one embodiment, the loop antenna 210 of antenna arrangement 200 may be utilized with an implantable device as an implantable antenna (e.g., antenna 120 of FIGS. 1 and 2). Advantageously, the loop antenna 210 may enable magnetic coupling of an implantable device (e.g., implantable device 105 of FIG. 1) to an external component (e.g., external component 160 of FIG. 1) for power and/or command signals and/or data signals) transference.

Figure 4:
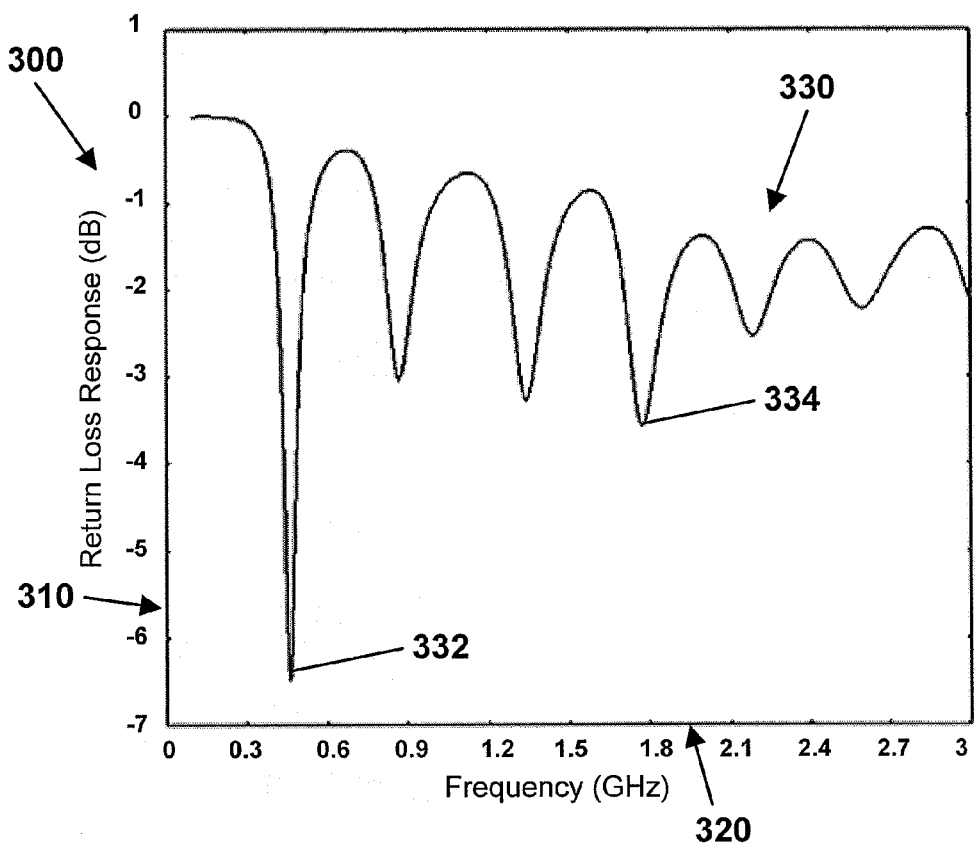
FIG. 4 is a first graph plotting the Return Loss Response of the unloaded loop antenna of the first antenna arrangement of FIG. 3 as a function of frequency in accordance with the principles of the present disclosure as described herein.

FIG. 4 is a first graph 300 plotting a Simulated Return Loss Response 330 of the first port 211 of the first antenna arrangement 200 as a function of frequency. The results plotted in the first graph 300 were obtained using a mathematical model (i.e., numerical simulation) of a loop antenna in free space separate from an implantable device. Accordingly, the first graph 300 (i.e., as well as the graphs shown in FIGS. 6, 8, 10, and 12) are provided to disclose the relative RF radiation capability of each antenna arrangement with respect to each other and not to describe the actual radiation capability of the implantable system.

The first graph 300 includes a first axis 310 representing the Return Loss Response (dB) of the loop antenna 210 as measured at the first port 211. The first axis 310 ranges from about −7 decibels (dB) to about 1 dB. The first graph 300 also includes a second axis 320 representing the frequency of the loop antenna 210. The second axis 320 ranges from about 0 gigahertz (GHz) to about 3 GHz. As shown in the first graph 300, the Return Loss Response 330 has a first dip 332 of about −6.5 dB at a frequency of approximately 0.45 GHz. Additional dips (e.g., see 334) occur at higher signal frequencies. This configuration may be desirable if a low resonant frequency and/or a lower amplitude, high resonant frequency is desired. As the amplitude of the dips in FIG. 4 tends to be lower than in other configurations described herein, the radiation capability of this configuration is lesser than some of the other configurations.

Figure 5:
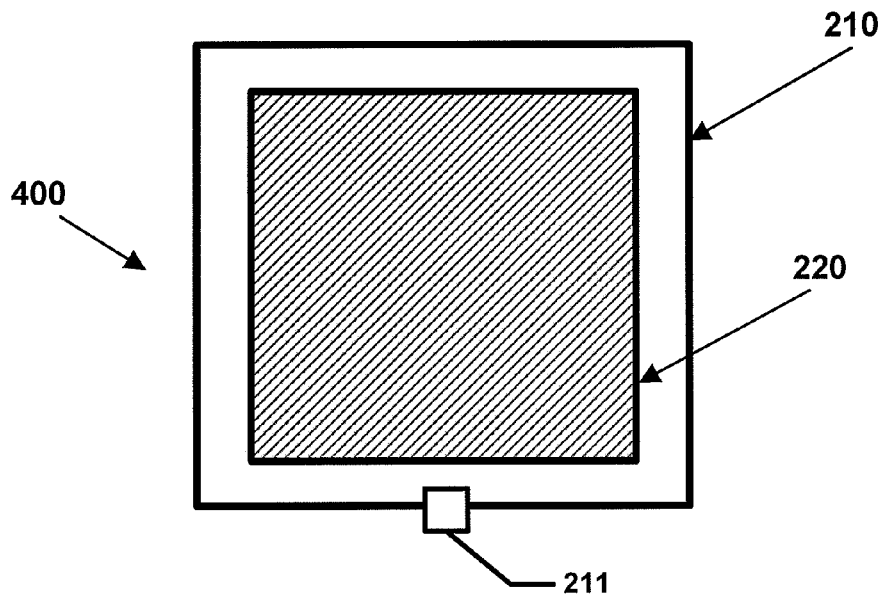
FIG. 5 is a schematic block diagram of another example antennae arrangement including a loaded loop antenna in accordance with the principles of the present disclosure as described herein.

FIG. 5 is a schematic block diagram of a second example antenna arrangement 400 including a loaded loop antenna that may be used in the implantable devices disclosed herein. The second antenna arrangement 400 includes the loop antenna 210 of FIG. 1 and a floating conductive plate 220 providing a loading effect on the loop antenna 210. For example, the effects of the conductive plate 220 can represent the loading effects of a conductive housing on an antenna arrangement in an implantable device. The loop antenna 210 has the first port 211 and is wound one or more times around the plate 220 without contacting the plate 220.

Figure 6:
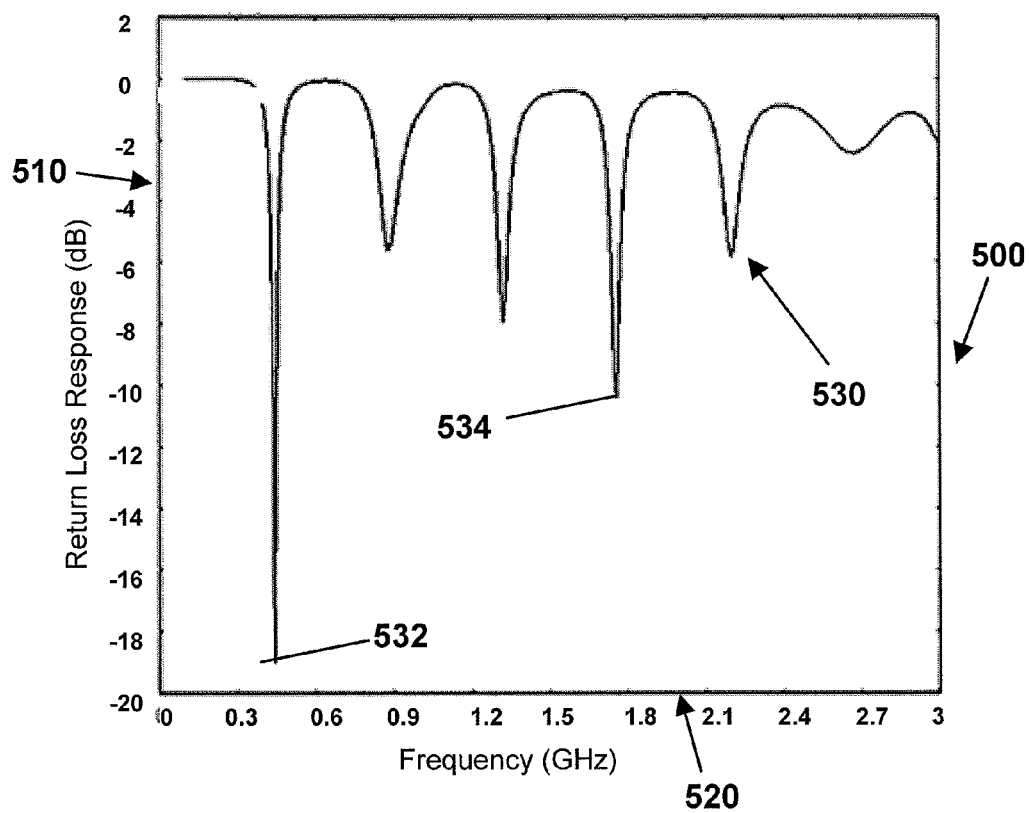
FIG. 6 is a second graph plotting the Return Loss Response of the loaded loop antenna of the second antenna arrangement of FIG. 5 as a function of frequency in accordance with the principles of the present disclosure as described herein.

In general, the plate 220 affects the Return Loss Response of the loop antenna 210 (e.g., through "the loading effect") as shown in FIG. 6. The effects of the housing 106 of the implantable device 105 on the implantable antenna 120 (see FIG. 1) mimic these effects of the floating conductive plate 220 on the loop antenna 210.

FIG. 6 is a second graph 500 plotting the Return Loss Response 530 of the first port 211 of the second antenna arrangement 400 as a function of frequency. The second graph 500 is provided to aid in comparing the radiation capability of the loaded loop antenna arrangement 400 to other antenna arrangement (e.g., the unloaded loop antenna arrangement 200 of FIG. 3) disclosed herein. The results plotted in the second graph 500 were obtained using a mathematical model (i.e., numerical simulation) of a loaded loop antenna in free space separate from an implantable device.

The second graph 500 includes a first axis 510 representing the Return Loss Response at the first port 211 of the loaded loop antenna arrangement 400. The first axis 510 ranges from about −20 dB to about 2 dB. The second graph 500 also includes a second axis 520 representing the frequency of the loaded loop antenna arrangement 400. The second axis 520 ranges from about 0 GHz to about 3 GHz. As shown in the second graph 500, the Return Loss Response 530 has a dip 532 of about −19 dB at a frequency of approximately 0.5 GHz. Additional dips (e.g., see 534) occur at higher signal frequencies.

Accordingly, loading the loop antenna 210 of the first antenna arrangement 200 with a conductive plate 220, as shown in FIG. 5, increases the radiation capability of the antenna arrangement. The amplitude of the dips (e.g., dips 532, 534) in the Return Loss Response 530 has increased. However, the dips in the Simulated Return Loss Response 530 did not shift significantly on the second axis 520. Accordingly, the frequency (i.e., or frequencies) at which the antenna arrangement resonates is not significantly affected.

Figure 7:
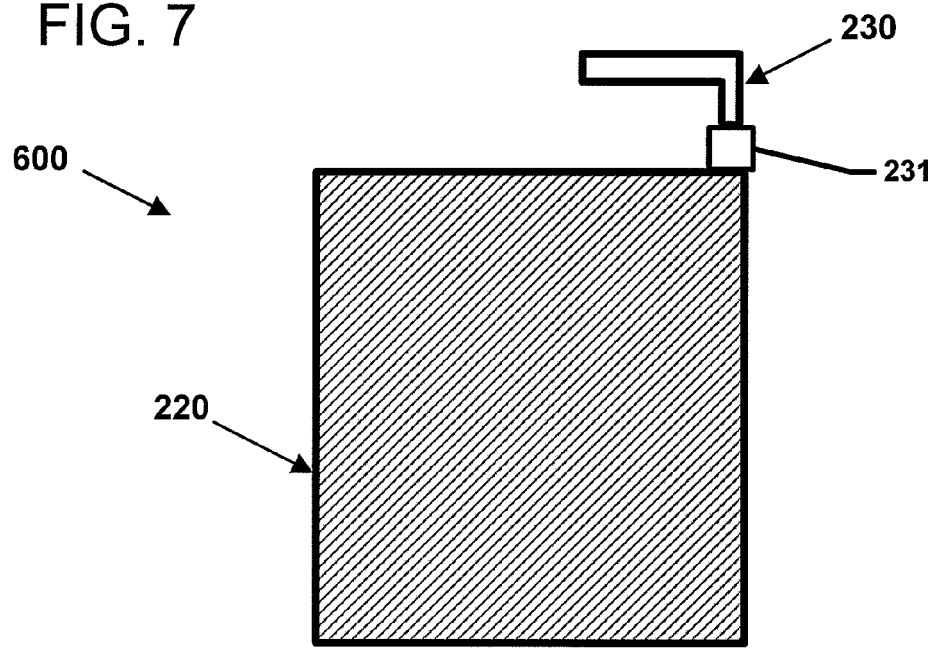
FIG. 7 is a schematic block diagram of a third antennae arrangement including an unbalanced antenna in accordance with the principles of the present disclosure as described herein.

FIG. 7 is a schematic block diagram of a third antenna arrangement 600 including an unbalanced antenna 230 capacitively coupled to a conductive plate, such as conductive plate 220 of FIG. 5, that may be used in the implantable devices disclosed herein. The unbalanced antenna 230 has a port 231. In the example shown, the unbalanced antenna 230 includes an inverted-L antenna arranged adjacent to the conductive plate 220. In other embodiments, however, the unbalanced antenna 230 may include any unbalanced antenna. Non-limiting examples of a suitable unbalanced antenna 230 include a helical antenna, a spiral antenna, a zigzag antenna, a folded antenna, and a serpentine antenna.

Figure 8:
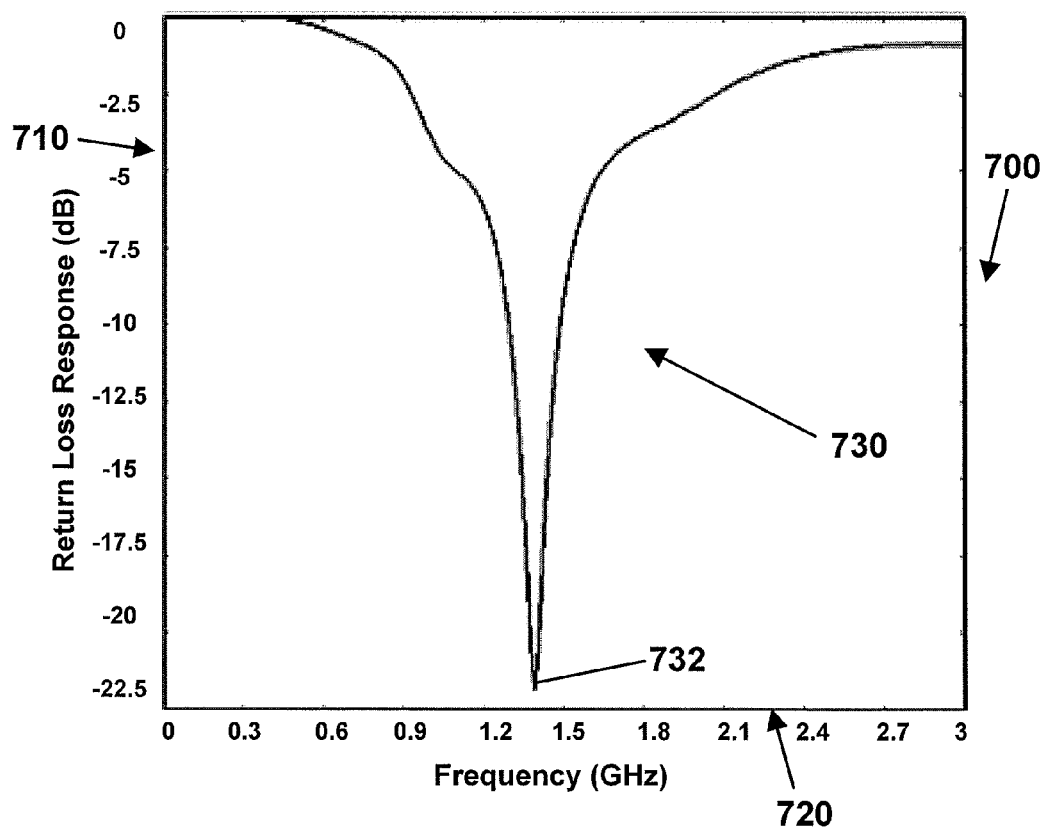
FIG. 8 is a third graph plotting the Return Loss Response of the unbalanced antenna of the third antenna arrangement of FIG. 7 as a function of frequency in accordance with the principles of the present disclosure as described herein.

FIG. 8 is a third graph 700 plotting the Return Loss Response 730 at the port 231 of the third antenna arrangement 600 as a function of frequency. The third graph 700 is provided to aid in comparing the radiation capability of the antenna arrangement 600 to other antenna arrangements (e.g., the loaded loop antenna arrangement 400 of FIG. 5) disclosed herein. The results plotted in the third graph 700 were obtained using a mathematical model (i.e., numerical simulation) of an inverted-L antenna arranged in free space separate from an implantable device.

The third graph 700 includes a first axis 710 representing the Return Loss Response at the port 231 of the third antenna arrangement 600. The first axis 710 ranges from about −22.5 dB to about 0 dB. The third graph 700 also includes a second axis 720 representing the frequency of the third antenna arrangement 600. The second axis 720 ranges from about 0 GHz to about 3 GHz. As shown in the third graph 700, the Return Loss Response 730 at the port 231 has a dip 732 of about −22 dB at a frequency of approximately 1.4 GHz.

As shown in FIG. 8, the third antenna arrangement 600 including the unbalanced antenna 230 radiates more effectively at a higher operating frequency (i.e., has a higher resonant frequency) than the loop antenna arrangements 200, 400 disclosed above. Accordingly, the third antenna arrangement 600 is capable of transmitting over a greater distance.

Figure 9:
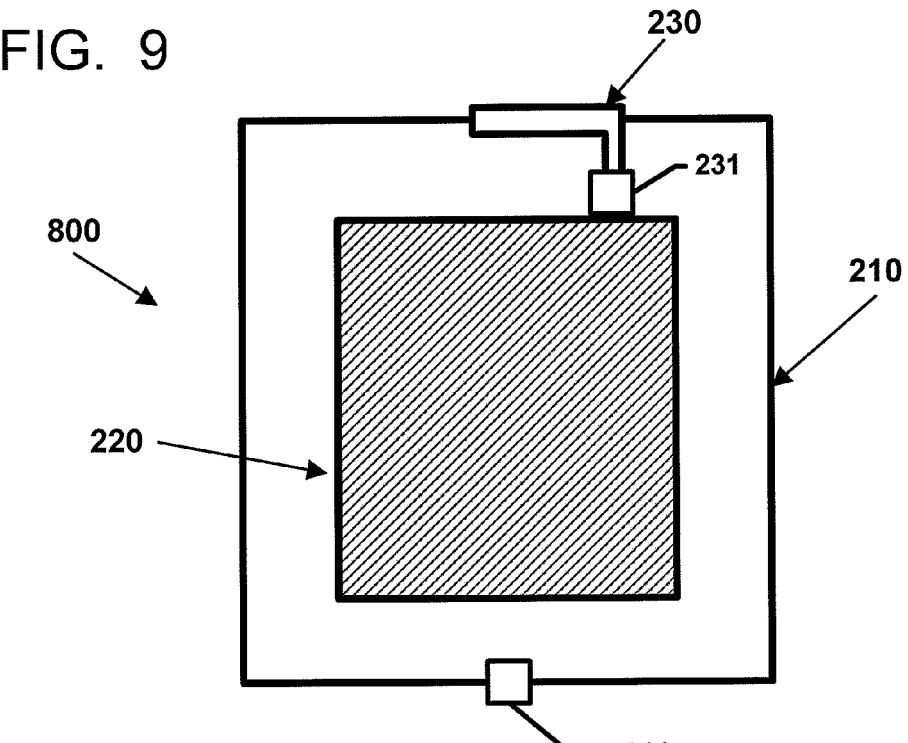
FIG. 9 is a schematic block diagram of a fourth example antenna arrangement including an unbalanced antenna capacitively coupled to a loaded loop antenna in accordance with the principles of the present disclosure as described herein.

Referring to FIGS. 9-12, providing an antenna arrangement including two or more antennae may enhance the efficiency of the implantable device. FIG. 9 is a schematic block diagram of an example antenna arrangement 800 that may be used in the implantable devices disclosed herein. In general, the antenna arrangement 800 capacitively couples the loaded loop antenna 400 of FIG. 5 with the unbalanced antenna 600 of FIG. 7. Accordingly, the fourth antenna arrangement 800 includes the loop antenna 210, the conductive plate 220, and the unbalanced antenna 230 disclosed herein. In the example shown in FIG. 9, the unbalanced antenna 230 is an inverted-L antenna. In other embodiments, however, the unbalanced antenna 230 may includes any suitable unbalanced antenna arranged to capacitively couple to the plate 220 and to the loop antenna 210.

Figure 10:
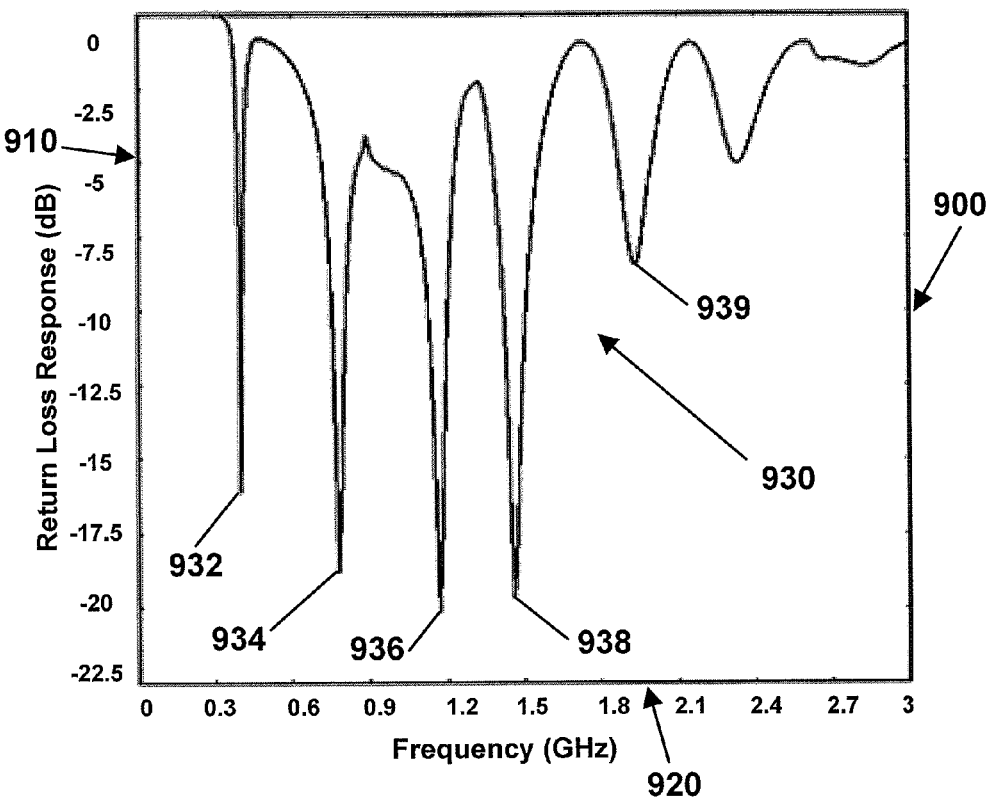
FIG. 10 is a fourth graph plotting the Return Loss Response of the unbalanced antenna of the fourth antenna arrangement of FIG. 9 as a function of frequency in accordance with the principles of the present disclosure as described herein.

Each of the antennae 210, 230 has its own port 211, 231, respectively, at which the Return Loss Response of the antenna 400, 600 may be simulated. FIG. 10 is a fourth graph 900 plotting the Simulated Return Loss Response 930 at the first port 211 of the loop antenna 210 of the fourth antenna arrangement 800 as a function of frequency. Accordingly, the Simulated Return Loss Response 930 indicates how capacitively coupling the unbalanced antenna to the loop antenna affects the radiation capability of the loop antenna 210.

The fourth graph 900 is provided to aid in comparing the radiation capability of the fourth antenna arrangement 800 to other antenna arrangement (e.g., the loaded loop antenna arrangement 400 of FIG. 5 and/or the unbalanced antenna arrangement 600 of FIG. 7) disclosed herein. The results plotted in the fourth graph 900 were obtained using a mathematical model (i.e., numerical simulation) of an inverted-L antenna capacitively coupled to a loaded loop antenna in free space separate from a communications circuit or other part of an implantable device.

The fourth graph 900 includes a first axis 910 representing the Return Loss Response at port 231 of the unbalanced antenna 230 of the fourth antenna arrangement 800. The first axis 910 ranges from about −22.5 dB to about 0 dB. The fourth graph 900 also includes a second axis 920 representing the frequency of the fourth antenna arrangement 800. The second axis 920 ranges from about 0 GHz to about 3 GHz. As shown in the fourth graph 900, the Return Loss Response 930 has a first dip 932 of about −16 dB at a frequency of approximately 0.4 GHz, a second dip 934 of about −19 dB at about 0.75 GHz, a third dip 936 of about −20 dB at about 1.2 GHz, and a fourth dip 938 of about −19.5 dB at about 1.5 GHz. Additional dips occur at higher signal frequencies (e.g., see dip 939).

A comparison of the second, third, and fourth graphs 500, 700, 900, respectively, indicates that capacitively coupling an unbalanced antenna (e.g., unbalanced antenna 230 of FIG. 7) to a loaded loop antenna (e.g., loaded loop antenna 210 of FIG. 5) yields an antenna arrangement with a greater aperture than either antenna individually. Advantageously, the resulting antenna arrangement has an increased radiation efficiency and increased resonance. In addition, the larger dips in the Simulated Return Loss Response at resonant frequencies in FIG. 10 also indicate the antenna arrangement may utilize less power to transmit over a given range or may transmit farther for a given power level.

Furthermore, increasing the aperture of the antenna may enable communication at MICS (Medical Implant Communications Service) frequency levels (e.g., about 0.4 GHz) and WMT (Wireless Medical Telemetry) frequencies levels (about 1.4 GHz) without a matching circuit. Eliminating the matching circuit from the implantable device would enable the implantable device to be smaller and manufactured at lower cost. Eliminating the matching circuit also may enhance the reliability of the implantable device by reducing the number of parts.

In addition, capacitively coupling an unbalanced antenna (e.g., unbalanced antenna 230 of FIG. 7) to a loaded loop antenna (e.g., loaded loop antenna 210 of FIG. 5) yields an antenna arrangement having an increased number of resonant frequencies. For example, the capactively coupled antenna arrangement 800 of FIG. 9 has a resonant frequency dip 932 at approximately 0.4 GHz and another resonant frequency dip 938 at about 1.5 GHz (see FIG. 10). In other embodiments, the antenna arrangement 800 could be configured to have a resonant frequency of about 6.7 MHz.

Increasing the number of resonant frequencies may increase the number of signals that may be obtained by the antenna arrangement. For example, the antenna arrangement, in one embodiment, a capacitively coupled antenna arrangement may be able to radiate power and communication signals. In one embodiment, increasing the number of resonant frequencies may increase the number of signals that may be obtained concurrently.

Furthermore, providing an antenna arrangement including multiple antennae enables each antenna to be configured to perform separate functions. For example, the antenna arrangement may include a first antenna (e.g., loop antenna 210) configured to radiate power and a second antenna (e.g., unbalanced antenna 230) configured to radiate communication signals. The first antenna may receive power (e.g., from about zero to about three watts) from one or more external components (e.g., see external component 160 of FIG. 2) and the second antenna may receive and transmit data (e.g., therapy parameters, treatment schedules, patient use data, treatment results, etc.) and/or commands (e.g., begin treatment, utilize a given treatment schedule, etc.) from and to the external components. In one embodiment, the received power is used to recharge an internal power source, such as rechargeable battery 117 of FIGS. 1 and 2. In other embodiments, however, a fewer or greater number of antennae may be utilized to receive and transmit communication signals and/or power signals.

Advantageously, by radiating power over a first antenna and communication signals over a second antenna, the power and communication signals may be radiated concurrently, thereby enhancing the efficiency of the implantable device. Furthermore, by separating which functions are performed by which antennae, each antenna may be tuned to optimize performance of its assigned task. For example, the first antenna may be a loop antenna configured to radiate high amplitude RF signals at lower frequencies (e.g., over shorter distances) and the second antenna may be an unbalanced antenna configured to radiate RF signals at higher frequencies (e.g., over longer distances). In such an embodiment, power may be transferred within the near-field of the antenna arrangement and communication signals may be communicated within the far-field of the antenna arrangement.

Figure 11:
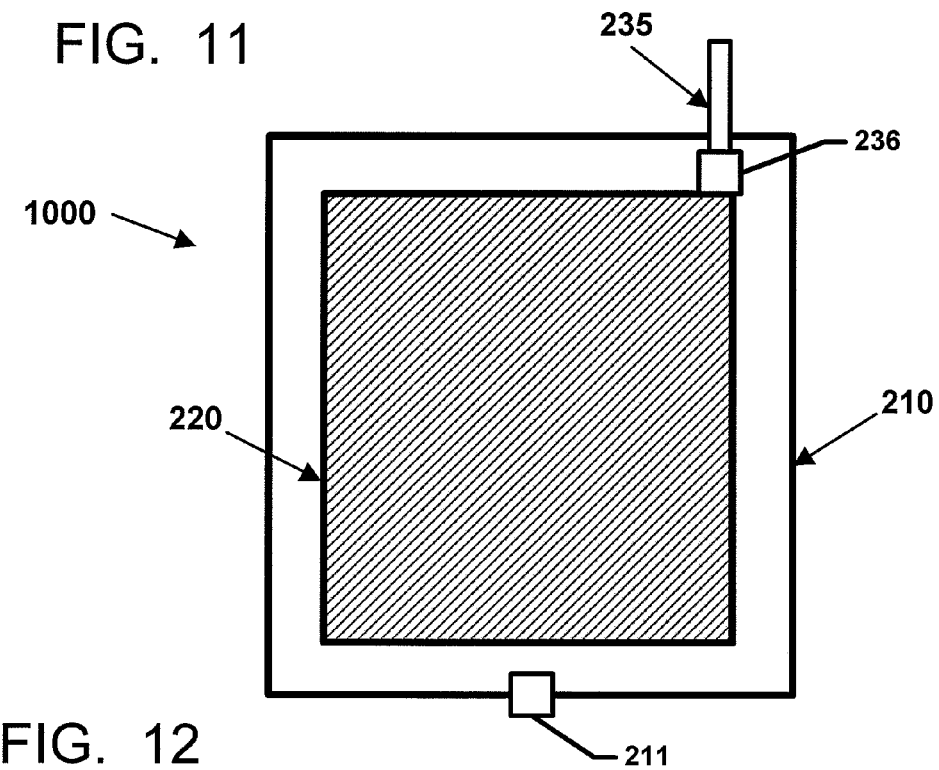
FIG. 11 is a schematic block diagram of a fifth example antenna arrangement including an unbalanced antenna decoupled from a loaded loop antenna in accordance with the principles of the present disclosure as described herein.

Decoupling antennae of an antenna arrangement also may provide advantages. FIG. 11 is a schematic block diagram of a fifth example antenna arrangement 1000 that may be used in the implantable devices disclosed herein. The fifth antenna arrangement 1000 includes a loop antenna 210 loaded with a conductive plate 220 and another unbalanced antenna 235. Both antennae 210, 235 have ports 211, 236, respectively, at which Return Loss Response may be measured. The unbalanced antenna 235 of the fifth antenna arrangement 1000, however, is decoupled from the loop antenna 210 (e.g., arranged perpendicular to the loop antenna 210). In the example shown in FIG. 11, the unbalanced antenna 235 is a vertical monopole antenna. In other embodiments, however, the unbalanced antenna 235 may include any suitable antenna arranged to not couple to the loop antenna 210.

Figure 12:
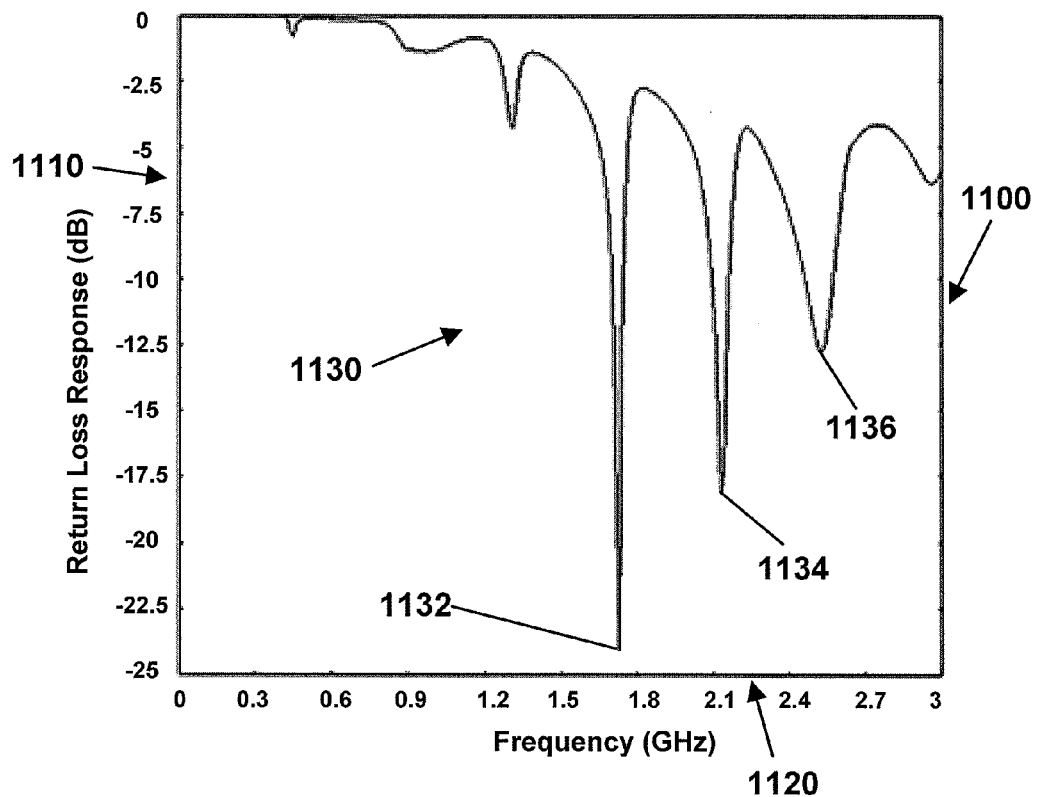
FIG. 12 is a fifth graph plotting the Return Loss Response of the unbalanced antenna of the fifth antenna arrangement of FIG. 11 as a function of frequency in accordance with the principles of the present disclosure as described herein.

FIG. 12 is a fifth graph 1100 plotting the Return Loss Response 1130 at the port 236 of the decoupled monopole antenna 235 of the fifth antenna arrangement 1000 as a function of frequency. The fifth graph 1100 is provided to aid in comparing the radiation capability of the decoupled antenna arrangement 1000 to other antenna arrangement (e.g., the antenna arrangement 800 of FIG. 9) disclosed herein. The results plotted in the fifth graph 1100 were obtained using a mathematical model (i.e., numerical simulation) of a monopole antenna decoupled from a loaded loop antenna in free space separate from an implantable device.

The fifth graph 1100 includes a first axis 1110 representing the Return Loss Response at the port 236 of the unbalanced antenna 235 of the fifth antenna arrangement 1000. The first axis 1110 ranges from about −25 dB to about 0 dB. The fifth graph 1100 also includes a second axis 1120 representing the frequency of the fifth antenna arrangement 1000. The second axis 1120 ranges from about 0 GHz to about 3 GHz. As shown in the fifth graph 1100, the Return Loss Response 1130 of the decoupled antenna arrangement 1000 has a first dip 1132 of about −24 dB at a frequency of approximately 1.7 GHz, a second dip 1134 of about −18 dB at about 2.1 GHz, and a third dip 1136 of about −13 dB at about 2.5 GHz.

Accordingly, decoupling an unbalanced antenna (e.g., antenna 235) from a loaded loop antenna (e.g., loaded loop antenna 210) shifts the resonant frequencies of the antenna arrangement to higher frequencies (e.g., compare FIGS. 6, 8, and 12). Decoupling the antennae also may decrease the number of resonant frequencies. Advantageously, decreasing the number of resonant frequencies may mitigate interference between different antennae. For example, decoupling the antennae may enable simultaneous radiation of power signals and communication signals by different antennae without interference.

Insulating the Antenna Arrangements

Referring now to FIGS. 13-23, the radiation capability of different antenna configurations (balanced antenna configurations and/or unbalanced antenna configurations) may be modified by partially or fully embedding one or more of the antennae in an insulating layer of dielectric material. Non limiting examples of insulating dielectric materials include biocompatible materials, such as biocompatible plastics (e.g., silicone rubber, polysulphone, TECOTHANE® offered by Lubrizol Advanced Materials, Inc. of Cleveland, Ohio, etc).

FIGS. 13-18 are schematic block diagrams illustrating different embodiments of an implantable device 1200A, 1200B, 1200C, 1200D, 1200E, 1200F, respectively, having an antenna arrangement including a loop antenna 1210 loaded with a conductive medium 1220. In one embodiment, the conductive medium 1220 includes the hermetically sealed inner housing of an implantable device that contains the circuitry of the implantable device. In other embodiments, however, the conductive medium 1220 may include any conductive surface. In the examples shown in FIGS. 13-18, the loaded loop antenna 1210 enters the inner housing 1220 and couples to components within the housing 1220 via an antenna port 1211.

Figure 13:
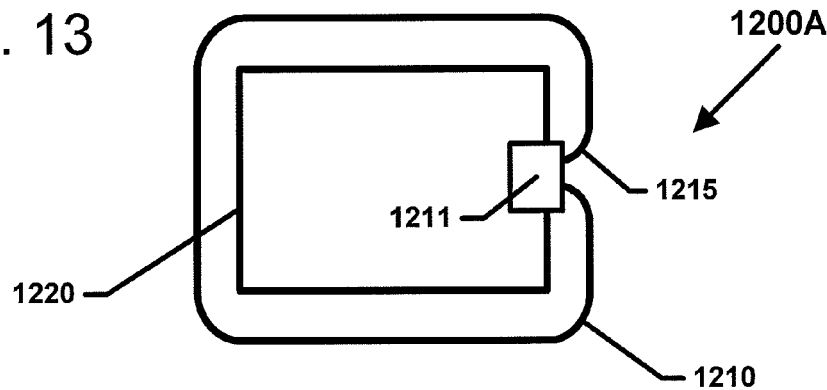
FIG. 13 is a schematic block diagram of an implantable device including a loop antenna wound around a housing and entering the housing at a first port in accordance with the principles of the present disclosure as described herein.

In FIG. 13, the antenna arrangement of the implantable device 1200A is fully exposed (i.e., no part of the antenna arrangement is enclosed within a dielectric medium). Accordingly, antenna arrangement may be arranged in contact with surrounding tissue when implanted within a patient. Non-limiting examples of surrounding tissue may include muscle, fat, nerve, or skin layers of the patient. In the example shown, the antenna arrangement includes a loaded loop antenna 210. In other embodiments, however, the antenna arrangement may include one or more balanced and/or unbalanced antennae.

Advantageously, the dielectric constant of the surrounding tissue increases the aperture of the exposed antenna. Increasing the aperture of the antenna enables a smaller antenna to be utilized. Furthermore, radiating the loop antenna 1210 at lower frequencies (e.g., about 0.4 GHz) mitigates radiation efficiency concerns due to return loss, since human tissue tends to be low loss at these lower frequencies. Moreover, the antenna arrangement may cost less and/or be easier to manufacture without a dielectric layer.

Figure 14:
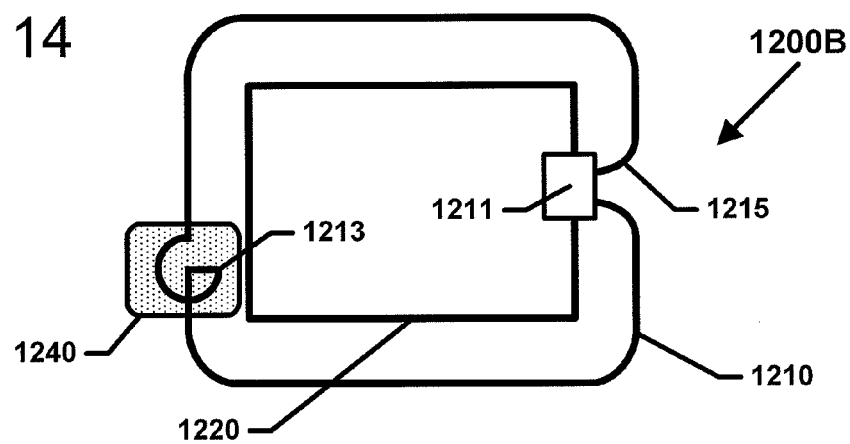
FIG. 14 is a schematic block diagram of an implantable device including and a loop antenna having a sharp edge embedded within a dielectric material in accordance with the principles of the present disclosure as described herein.
Figure 15:
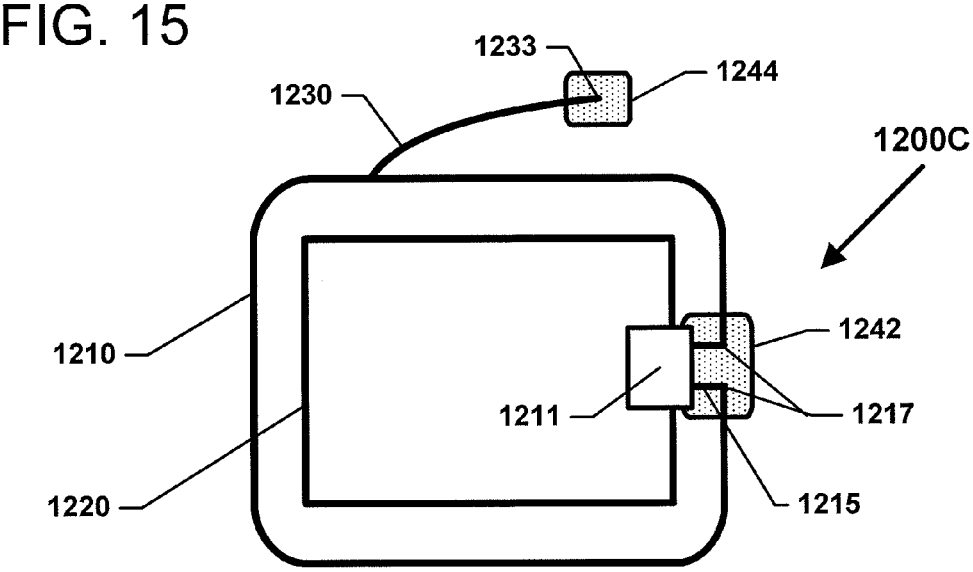
FIG. 15 is a schematic block diagram of an implantable device including and a loop antenna and an unbalanced antenna having a sharp edge embedded within a dielectric material in accordance with the principles of the present disclosure as described herein.

In FIGS. 14 and 15, sharp edges of the antenna arrangements of the implantable devices 1200B, 1200C may be partially embedded within an insulating dielectric medium. In FIG. 14, the antenna arrangement includes a loop antenna 1210 having a first sharp edge 1213 that is embedded within a dielectric layer 1240. In FIG. 15, the antenna arrangement includes a loop antenna 1210 having sharp corners 1217 that are embedded within a first dielectric layer 1242 and an unbalanced antenna 1230 having a sharp edge 1233 that is embedded within a second dielectric layer 1244. In other embodiments, however, the antenna arrangement may include a greater or fewer number of balanced and/or unbalanced antennae.

Portions of the loaded loop antenna 1210 still may be arranged in contact with surrounding tissue when implanted, thereby increasing the aperture of the antenna arrangements. Advantageously, however, insulating the sharp edges of the antenna arrangements may inhibit burns or other harm to a patient in which the antenna arrangement is implanted when the patient is scanned with a Magnetic Resonance Image (MRI) machine. If the sharp edges are left exposed, current induced by the magnetic field that is generated by the MRI machine may build up at these edges and burn the surrounding tissue. The low dielectric medium (e.g., dielectric layers 1240, 1242, 1244) may inhibit accumulation of a high current density at the antenna edges from the effects of the magnetic field created by the MRI machine.

Figure 16:
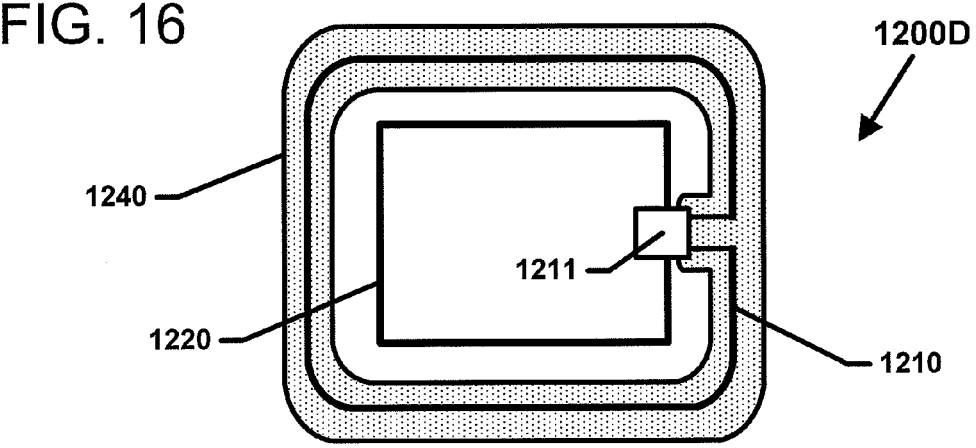
FIG. 16 is a schematic block diagram of an implantable device including a loop antenna fully embedded within a dielectric material and wound around a housing in accordance with the principles of the present disclosure as described herein.

In FIG. 16, the antenna arrangement of the implantable device 1200D is fully embedded within a layer of dielectric medium 1240. In the example shown, the antenna arrangement includes the loaded loop antenna 210. In other embodiments, however, the antenna arrangement may include one or more balanced and/or unbalanced antennae. After implantation, the implantable device 1200D may contact different types of surrounding tissue (e.g., fat, muscle, nerves, etc.). Each type of surrounding tissue may have different dielectric constants.

Embedding the antenna arrangement in the layer of dielectric medium insulates the antenna arrangement from effects of the dielectric constant of the surrounding medium. Accordingly, insulating the antenna arrangement in the dielectric material advantageously may enhance repeatability of performance by providing surrounding media (e.g., the dielectric layer 1240) having a consistent dielectric constant. Furthermore, when operating at higher frequencies (e.g., about 1.4 GHz), human tissue tends to be lossy (i.e., higher frequency signals tend to degrade as they travels through human tissue). Accordingly, insulating the antenna arrangement from the surrounding tissue may enhance the radiation efficiency of the antenna arrangement at higher frequencies. Moreover, if the dielectric layer is formed from a biocompatible material, then embedding the antenna arrangement within the dielectric layer may enhance the biocompatibility of the antenna arrangement.

Figure 17:
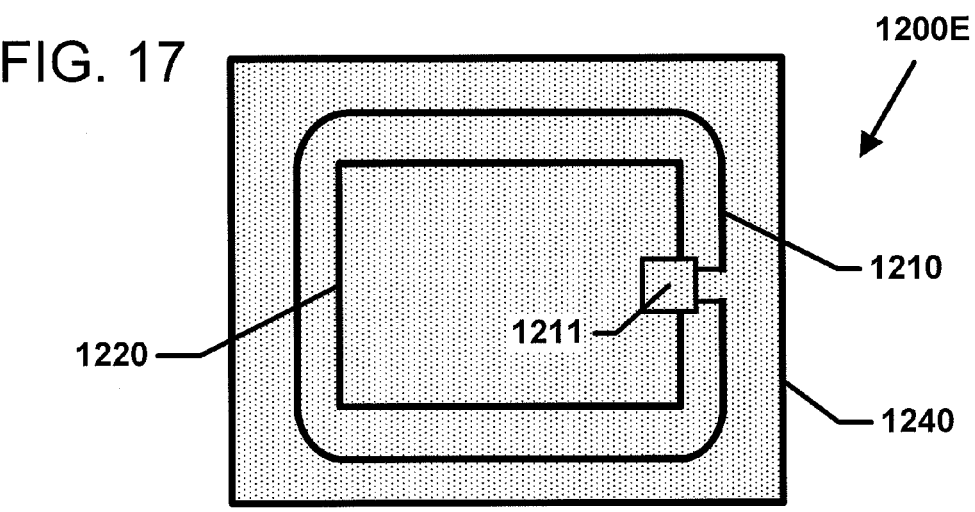
FIG. 17 is a schematic block diagram of an implantable device including a loop antenna wound around a housing with both the loop antenna and the housing being fully embedded within a dielectric material in accordance with the principles of the present disclosure as described herein.

In FIG. 17, the dielectric layer 1240 extends over the inner housing 1220 as well as the antenna arrangement (e.g., loaded loop antenna 1210) of the fifth implantable device 1200E. Advantageously, embedding the inner housing 1220 within the dielectric layer 1240 may increase the aperture of the antenna arrangement. For example, embedding the inner housing 1220 that loads the loop antenna 1210 may increase the aperture of the loop antenna 1210 by inhibiting the surface current on the periphery of the inner housing 1220. Furthermore, embedding the inner housing 1220 within the dielectric layer 1240 also may improve the biocompatibility of the implantable device 1220.

Figure 18:
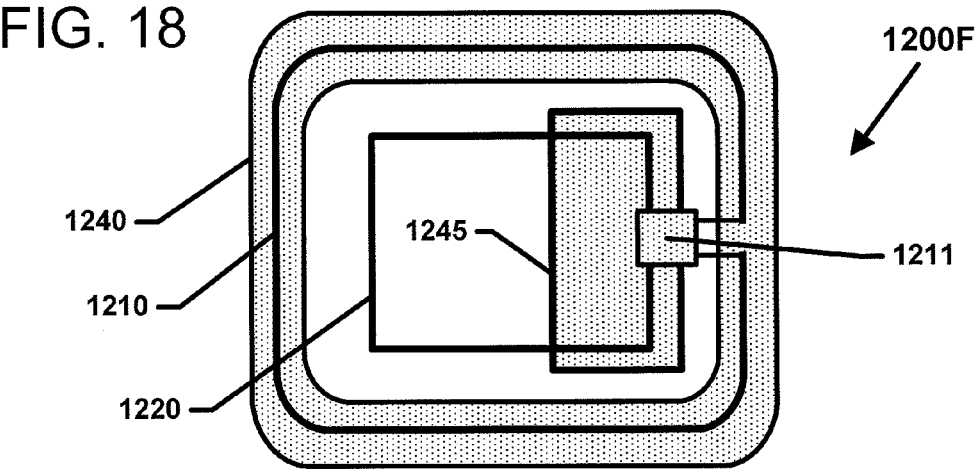
FIG. 18 is a schematic block diagram of an implantable device including a loop antenna wound around a housing with the loop antenna being fully embedded within a dielectric material and the housing being partially embedded within the dielectric material in accordance with the principles of the present disclosure as described herein.

In FIG. 18, a first dielectric layer 1240 extends over the antenna arrangement of the sixth implantable device 1200F and a second dielectric layer 1245 partially embeds the inner housing 1220. In one embodiment, the antenna arrangement includes a loaded loop antenna 1210. In other embodiments, however, the antenna arrangement may include one or more balanced and/or unbalanced antennae. Partially embedding the inner housing 1220 within a dielectric layer may increase the aperture of the antenna arrangement. In one embodiment, the section of the inner housing 1220 adjacent the port of the antenna arrangement (e.g., port 1211 of the loaded loop antenna 1210) may be embedded within a dielectric medium to increase the aperture of the antenna arrangement. Advantageously, exposed portions of the inner housing 1220 may be used to provide treatment to the patient (e.g., as an electrode).

Implantation environments for the antenna arrangement tend to vary by patient and even within the same patient. For example, the dielectric constant of tissue surrounding an antenna arrangement implanted within the patient may vary over the surface area of the antenna arrangement (e.g., when a first portion of the antenna arrangement contacts a nerve and a second portion of the antenna arrangement contacts muscle). Accordingly, to enhance understanding of the effects of the dielectric medium, the simulation is directed to a simple loop antenna 1310 arranged within a simplified implantation environment represented by a three-layer structure 1300 (see FIGS. 19-22).

In FIGS. 19-22, the three-layer structure 1300 includes an inner layer 1340 having a first dielectric constant $\epsilon 1$ arranged between two outer layers 1360, each of which have a second dielectric constant $\epsilon 2$. In general, the insulating layer 1340 represents a layer of dielectric medium (e.g., the dielectric layer 1240 shown in FIGS. 14-18) and the outer layers 1360 represent human tissue surrounding the implantable device. Accordingly, the first dielectric constant $\epsilon 1$ of the inner layer 1340 is less than the second dielectric constant $\epsilon 2$ of the outer layers 1360.

For ease in computation and understanding in the simulation, a thickness H of about 10 mm and a dielectric constant $\epsilon 1$ of about 1 were selected for the inner layer 1340 and a thickness T of about 150 mm and a dielectric constant $\epsilon 2$ of about 10 were selected for each of the outer layers 1360. These measurements do not necessarily represent preferred dimensions and properties of the antenna arrangement or of the implantation environment. Rather, these measurements provide a simple model from which a numerical simulation may be computed to facilitate explanation and testing of the concept. In other embodiments, the outer layers 1360 may have different dielectric constants and/or thicknesses from one another.

Figure 19:
FIG. 19 is a schematic block diagram of a simple loop antenna arranged in free space (i.e., completely outside the three-layer structure of FIG. 20) in accordance with the principles of the present disclosure as described herein.

FIG. 19 is a schematic block diagram of the loop antenna 1310 arranged within free space (i.e., completely outside the three-layer structure 1300). Accordingly, the loop antenna 1310 represents an implantable device having an antenna fully exposed to free space (e.g., air). For example, the loop antenna 1310 of FIG. 19 may represent an antenna arrangement of an implantable device before implantation.

Figure 20:
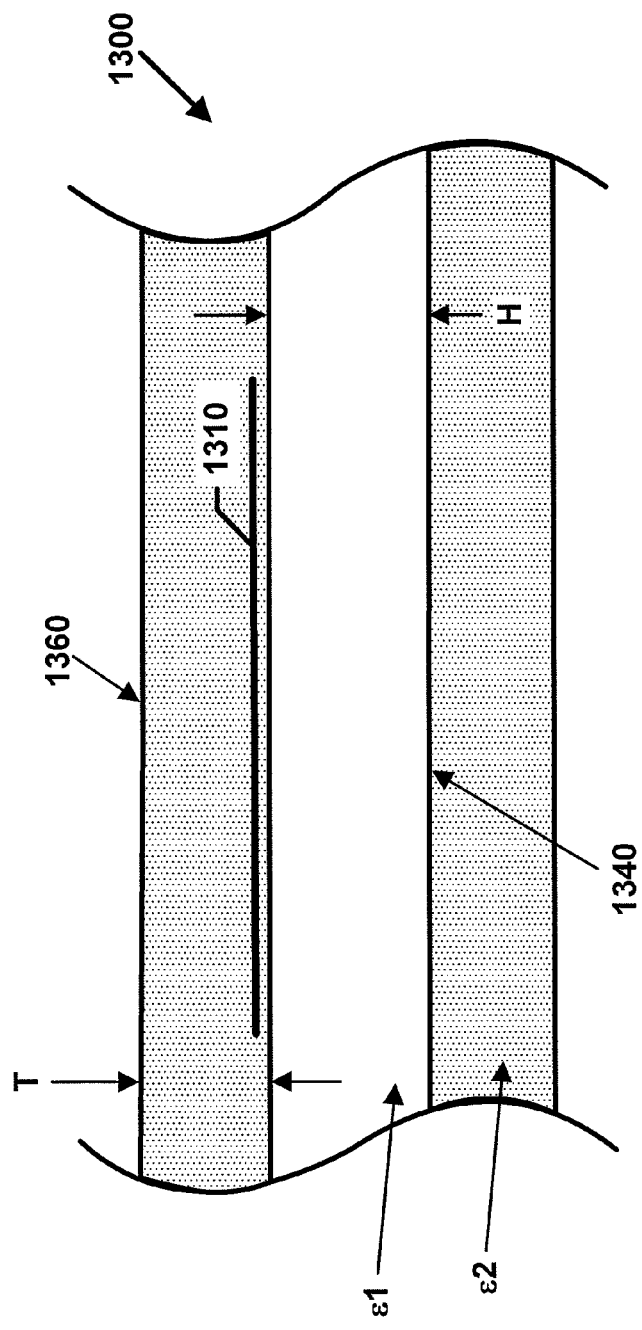
FIG. 20 is a schematic block diagram of a simple loop antenna arranged within an outer layer (and outside an insulating layer) of a three-layer structure in accordance with the principles of the present disclosure as described herein.

FIG. 20 is a schematic block diagram of the loop antenna 1310 arranged within one of the outer layers 1360 of the three-layer structure 1300 and outside the inner layer 1340. The loop antenna 1310 represents an implantable device having an antenna arrangement fully exposed to the surrounding tissue of the patient. For example, the loop antenna 1310 of FIG. 20 may represent the loaded loop antenna 1210 of FIG. 13, which is not insulated within an outer layer of a dielectric medium, after implantation.

Figure 21:
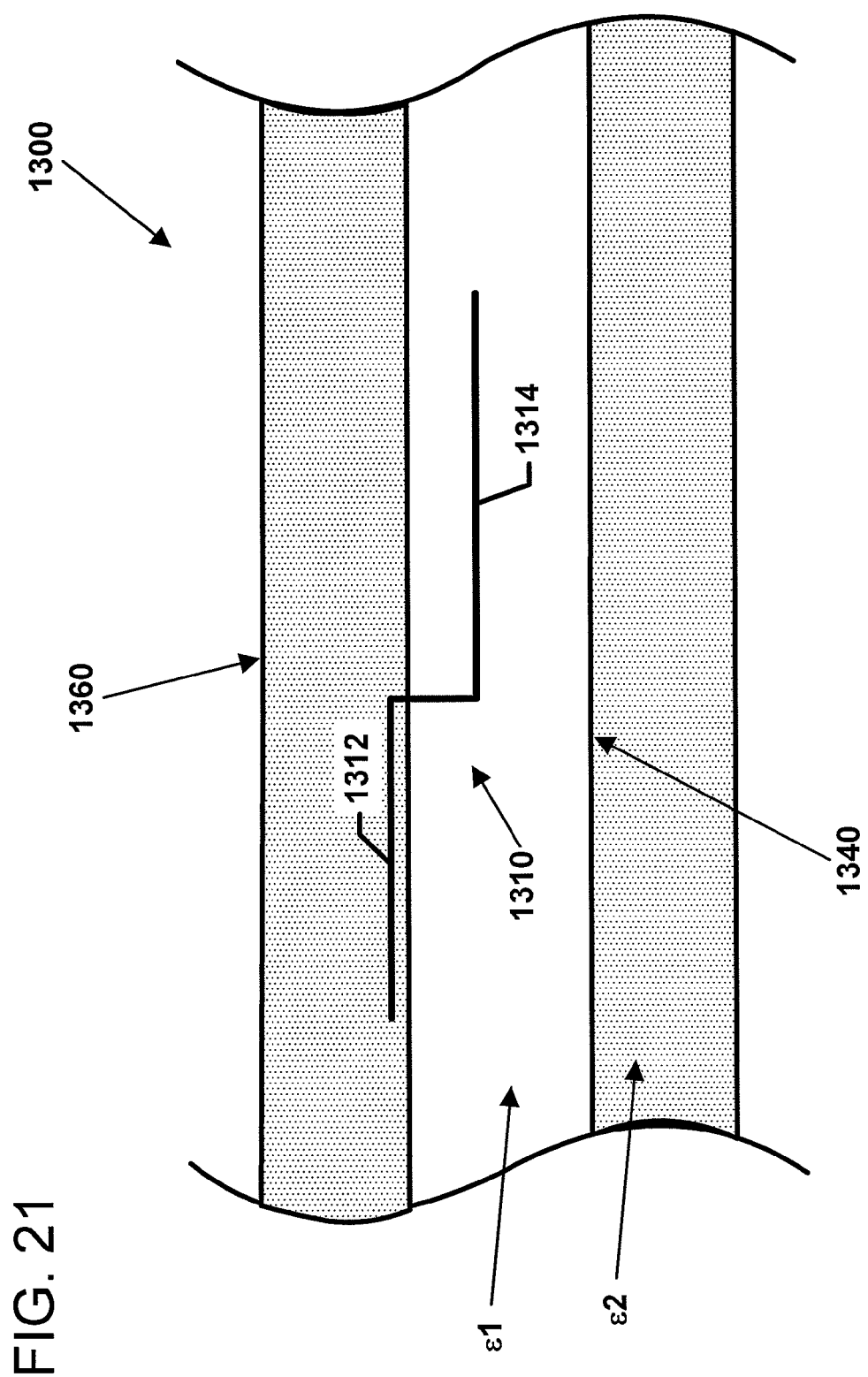
FIG. 21 is a schematic block diagram of a simple loop antenna having a first part arranged within an outer layer of the three-layer structure of FIG. 20 and a second part arranged within an insulating layer in accordance with the principles of the present disclosure as described herein.

FIG. 21 is a schematic block diagram of the loop antenna 1310 having a first part 1312 arranged within one of the outer layers 1360 and a second part 1314 arranged within the inner layer 1340. The loop antenna 1310 represents an implantable device having an antenna partially embedded within a dielectric medium and partially exposed to the surrounding tissue of the patient. For example, the loop antenna 1310 of FIG. 21 may represent the loaded loop antenna 1210 of FIG. 14, which is partially insulated within a layer 1240 of a dielectric medium, after implantation.

Figure 22:
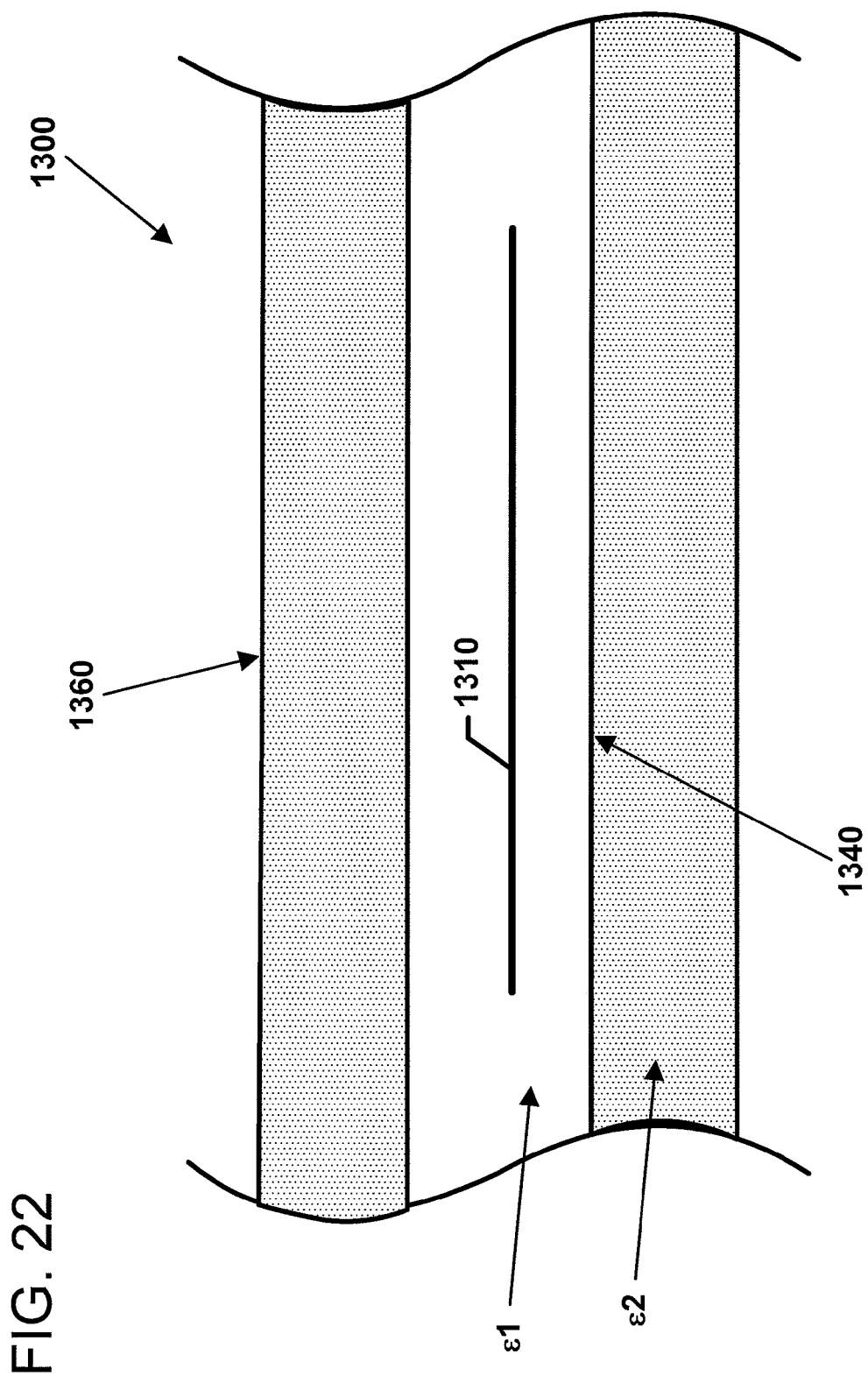
FIG. 22 is a schematic block diagram of a simple loop antenna arranged completely within an insulating layer of the three-layer structure of FIG. 20 in accordance with the principles of the present disclosure as described herein.

FIG. 22 is a schematic block diagram of the loop antenna 1310 arranged completely within the inner layer 1340. The loop antenna 1310 represents an implantable device having an antenna fully embedded within an insulating layer of dielectric medium. For example, the loop antenna 1310 of FIG. 22 may represent the loaded loop antenna 1210 of FIG. 16, which is fully insulated within a layer 1240 of a dielectric medium, after implantation.

Figure 23:
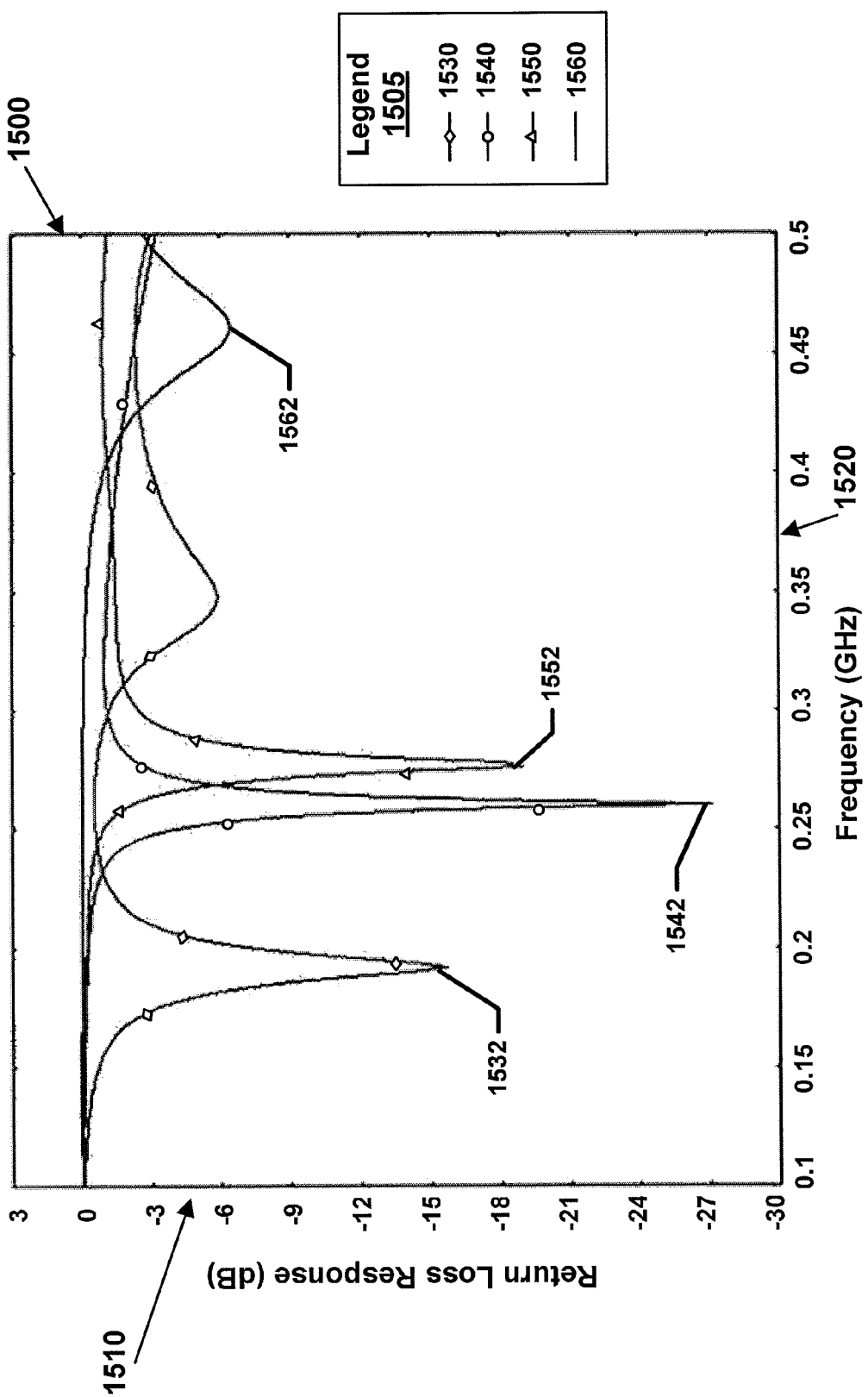
FIG. 23 is a graph plotting the lowest dip of a Return Loss Response of each of the loop antenna arrangements shown in FIGS. 19-22 as a function of frequency in accordance with the principles of the present disclosure as described herein.

The effects of the dielectric medium on the Return Loss Response of an example antenna arrangement are numerically simulated in FIG. 23 using computer modeling. FIG. 23 is a graph plotting the lowest dip of the Return Loss Response of the loop antenna 1310 for each arrangement shown in FIGS. 19-22 as a function of frequency. The graph 1500 has a first axis 1510 representing Return Loss Response (dB) and a second axis 1520 representing frequency. The first axis 1510 ranges from about −30 dB to about 3 dB and the second axis 1520 ranges from about 0.1 GHz to about 0.5 GHz. As noted in the legend 1505, symbols including circles, triangles, and diamonds have been added to the Return Loss Response curves of the graph 1500 to distinguish the different curves. These symbols do not correspond with actual data points, but rather serve only to differentiate the Return Loss Response curves.

The Return Loss Response 1560 of the loop antenna arranged in free space (FIG. 19) is depicted by the unembellished solid curve. The Return Loss Response 1560 of this arrangement provides a base reading to which the other Return Loss Responses may be compared. The Return Loss Response 1530 of the exposed loop antenna 1310 of FIG. 20 is depicted by the diamond-dotted curve. The Return Loss Response 1540 of the partially insulated loop antenna 1310 of FIG. 21 is depicted by the circle-dotted curve. The Return Loss Response 1550 of the fully insulated loop antenna 1310 of FIG. 22 is depicted by the triangle-dotted curve.

As shown in FIG. 23, the lowest resonant frequency of the loop antenna (unembellished curve) arranged in free space (see FIG. 19) is about 0.45 GHz with a return loss response 1560 of about −6 dB. The lowest resonant frequency of the exposed loop antenna (diamonds) (see FIG. 20) is about 0.19 GHz with a return loss response 1530 of about −16 dB. The lowest resonant frequency of the partially embedded loop antenna (circles) (see FIG. 21) is about 0.26 GHz with a return loss response 1540 of about −27 dB. The lowest resonant frequency of the fully embedded loop antenna (triangles) (see FIG. 22) is about 0.28 GHz with a return loss response 1550 of about −19 dB.

Accordingly, the graph 1500 indicates implanting an exposed loop antenna 1310 (FIG. 20) within human tissue lowers the resonant frequency and increases the radiation capability of the antenna arrangement (as compared to the antenna 1310 arranged in free space-FIG. 19).

Furthermore, partially embedding the loop antenna 1310 within an insulating layer of dielectric medium (FIG. 21) may shift the resonant frequency of the antenna to a higher frequency (compare curves 1530 and 1540). Fully embedding the loop antenna 1310 within the insulating layer of dielectric medium (FIG. 22) may further shift the resonant frequency of the antenna (compare curves 1540 and 1550).

Loop Antenna

Figure 34:
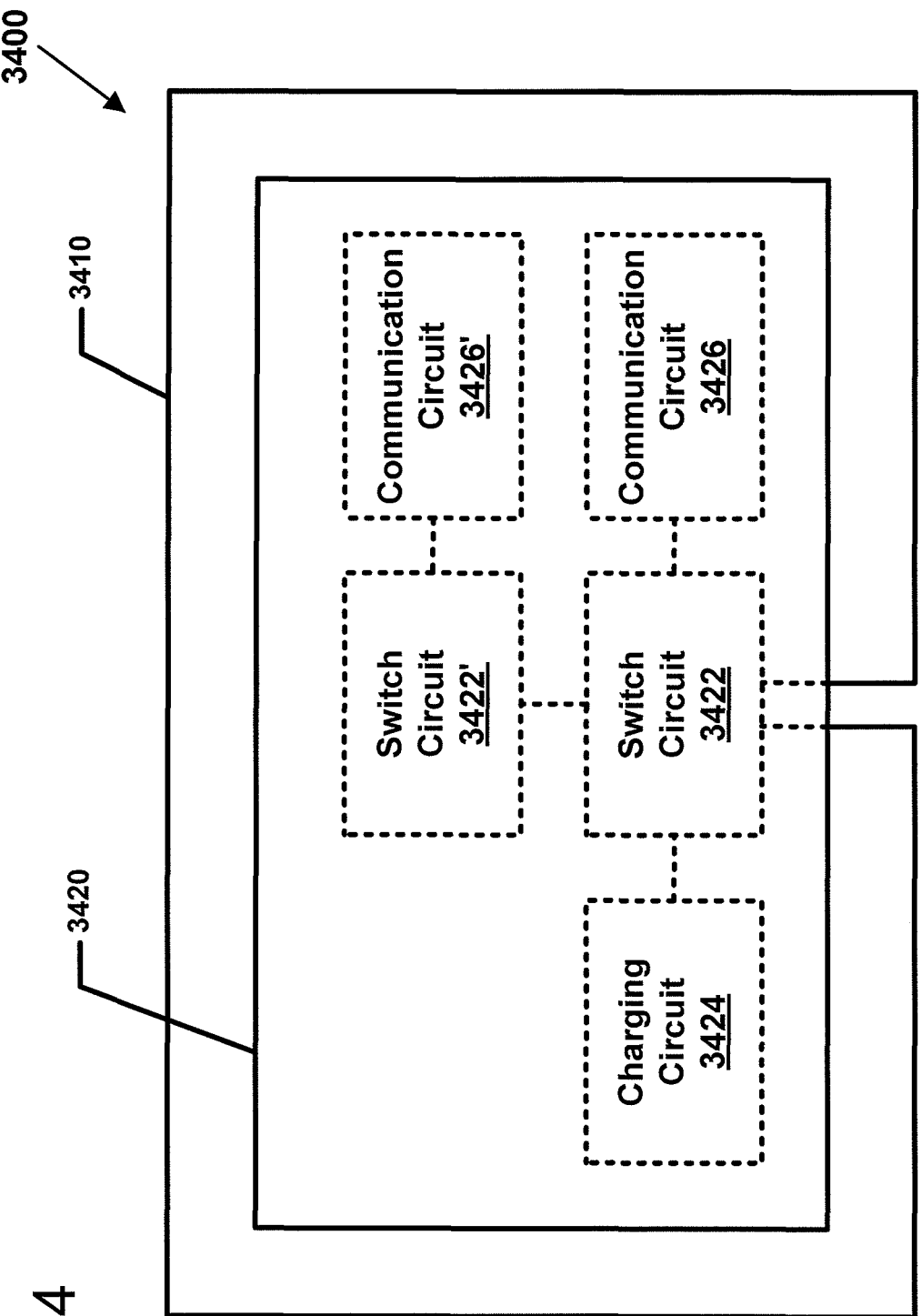
FIG. 34 is a schematic block diagram of an example implantable device including a loop antenna wound around a housing and configured in accordance with the principles of the present disclosure as described herein.

FIG. 34 is a schematic block diagram of an example implantable device 3400 including a loop antenna 3410 wound around a housing 3420. In one embodiment, the loop antenna 3410 is wound around the housing 3420 only about once. For example, the loop antenna 3410 has a length of at least λ, wherein λ is the effective wavelength for far-field data communications. In another embodiment, the loop antenna 3410 is wound around the housing 3420 multiple times. For example, in one embodiment, the loop antenna 3410 may be wound around the housing a sufficient number of times to have the antenna effective in near-field power transfer and/or communications. In one embodiment, the implantable device 3400 does not include a matching circuit.

In one embodiment, the loop antenna 3410 may be partially or fully embedded within a dielectric layer. In another embodiment, the loop antenna 3410 may be fully exposed to the environment in which the implantable device 3400 is arranged. In another embodiment, the housing 3420 may be partially or fully embedded in a dielectric material. In another embodiment, the housing 3420 may be fully exposed.

In general, the loop antenna 3410 is configured to receive power and to deliver the received power to circuitry within the housing 3420. In one embodiment, the loop antenna 3410 is configured to resonate when receiving and transmitting a low frequency signal (e.g., around 6.73 MHz). In such an embodiment, the loop antenna 3410 may deliver current induced by the received signal to a rechargeable power source 3424 within the housing 3420.

In another embodiment, the loop antenna 3410 is configured to resonate when receiving and transmitting a higher frequency signal (e.g., around 402-405 MHz). When the loop antenna 3410 resonates at higher frequencies, the loop antenna appears electrically larger than when the loop antenna 3410 resonates at lower frequencies. Accordingly, the loop antenna 3410 may receive and send far-field signals.

In such an embodiment, the loop antenna 3410 may deliver current induced by the received signal to a communications circuit (e.g., a MICS communications circuit) 3426 within the housing 3420. The loop antenna 3410 also may receive power from the rechargeable power source 3424 and a data or command signal from the communications circuit 3426 and transmit the data or command signal using the received power.

In another embodiment, the loop antenna 3410 is configured to resonate at multiple frequencies. In such an embodiment, the housing 3420 of the implantable device may include one or more switching circuits 3422 configured to receive current induced on the loop antenna 3410 when a signal is received. The switching circuit 3422 determines the type of signal received (e.g., based on the frequency) and may provide power to an appropriate circuit within the housing 3420 based on the type of signal received.

For example, in one embodiment, in the example shown in FIG. 34, the switching circuit 3422 is electrically coupled to the rechargeable power source 3424 and the communications circuit 3426 within the housing 3420. The switching circuit 3422 may determine whether to forward a signal received at the loop antenna 3410 to the power source 3424 for recharging or to the communications circuit 3426 for analysis. In another embodiment, the switching circuit 3422 may be electrically coupled to multiple communication circuits within the housing 3420. In such an embodiment, the switching circuit 3422 may determine the appropriate communication circuit to which to forward the received signal.

In other embodiments, additional circuitry may be provided within the housing 3420 and coupled to the switching circuit 3422 to provide additional functionality to the implantable device 3400. The switching circuit 3422 may direct power to the appropriate circuitry (e.g., based on the frequency of the received signal, based on instructions contained within the signal, etc.).

In one embodiment, inductive coupling between the loop antenna 3410 and one or more unbalanced antennae (e.g., see FIG. 24) increases the number of resonant frequencies of the loop antenna 3410. Accordingly, such inductive coupling may increase the range of applications capable of being performed by the implantable device 3400.

Antennae Array

An implantable device also may include an antenna arrangement including an array of antennae. For example, FIG. 24 is a schematic block diagram of an example embodiment of an implantable device 1600 including an inner housing 1620 coupled to an antennae arrangement 1650. The inner housing 1620 may contain an RF module and a treatment module as disclosed above with reference to FIGS. 1 and 2. The antenna arrangement 1650 includes a loop antenna 1610 coupled to an array 1660 of antennae that may include any combination of balanced and unbalanced antennae. In the example shown, the array 1660 includes antennae 1631-1639 coupled in series to the loop antenna 1610.

In general, the antennae array 1660 may enhance the flexibility and utility of the implantable device by providing radiation pattern diversity, spatial diversity, and/or polarization diversity. For example, each antenna within the antennae array 1660 may be tuned to resonate at a unique resonant frequency, thereby providing radiation pattern diversity. Different types of signals (e.g., power and communication) may be radiated over different frequency ranges. Spatial diversity of the antennae within the antennae array 1660 may enable an external component to identify a location of the implantable device. Polarization diversity may enhance coupling flexibility of the implantable device by reducing or removing dependencies of antenna orientation or antenna performance.

In some embodiments, two or more antennae of the array 1660 may be capacitively coupled to one another to increase the aperture of the antenna arrangement. In one embodiment, at least one of the antennae 1631-1639 of the antennae array 1660 is an unbalanced antenna. In other embodiments, one or more antennae of the array 1660 may be decoupled from the loop antenna 1610 to inhibit interference with radiation from other antennae, other components, and/or other devices.

The implantable device 1600 also may include an optional insulating layer 1640. In different embodiments, the insulating layer 1640 may partially or completely surround the antennae arrangement 1650. In the example shown in FIG. 24, the loop antenna 1610 and six of the additional antennae 1631-1636 of the array 1660 are fully embedded within the insulating layer 1640. Antennae 1637 and 1639 of the array 1660 are partially embedded within the insulating layer 1640 and antenna 1638 is fully exposed to any surrounding medium (e.g., air, tissue, etc.).

Example Applications

The above diagrams and numerical simulations provide the conceptual basis for understanding the following example embodiments of implantable devices configured in accordance with the principles of the present disclosure as described herein.

Figure 25:
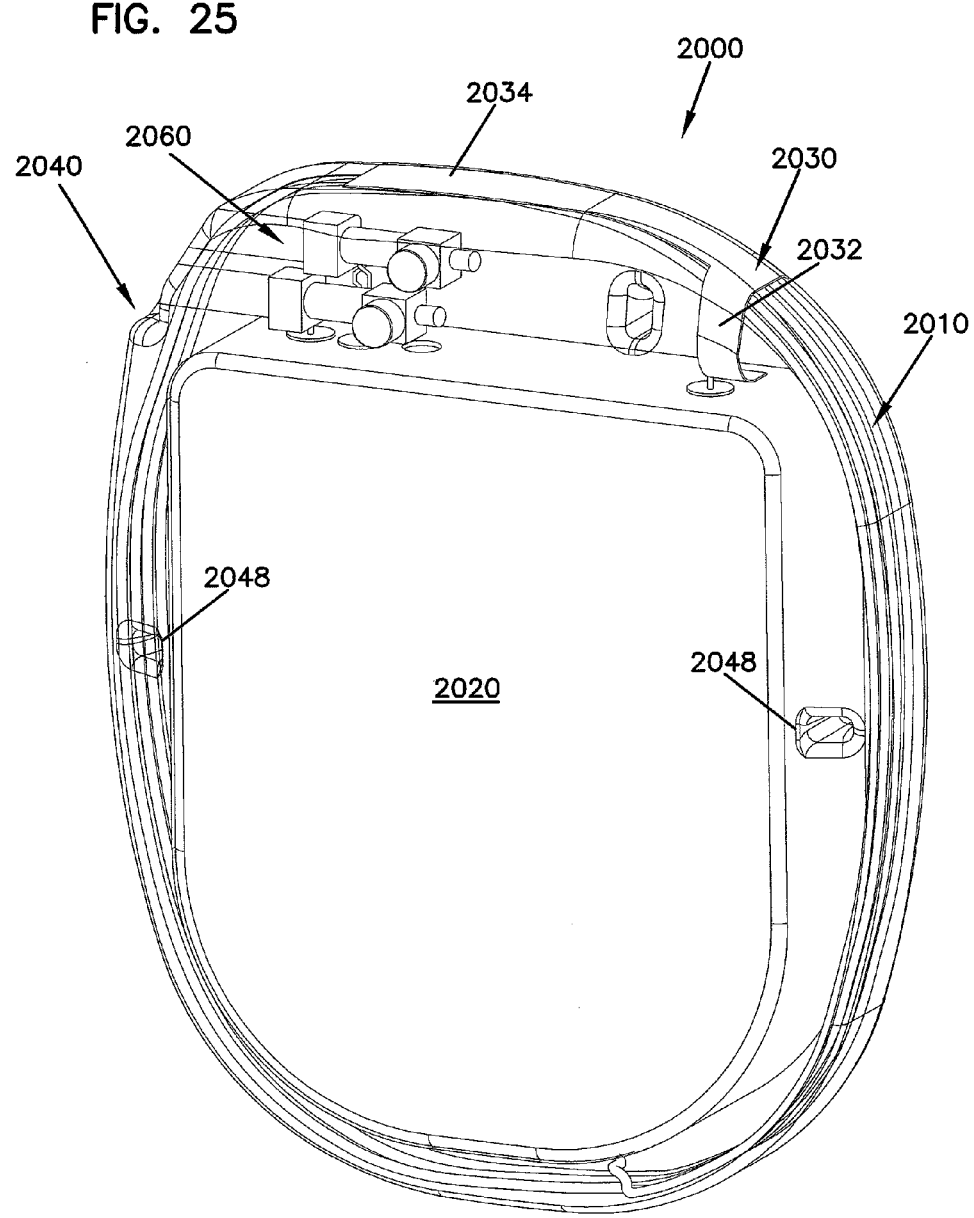
FIG. 25 is a perspective view of an implantable device having a loop antenna wrapped around an inner housing and capacitively coupled to a second antenna protruding from the inner housing in accordance with the principles of the present disclosure as described herein.
Figure 26:
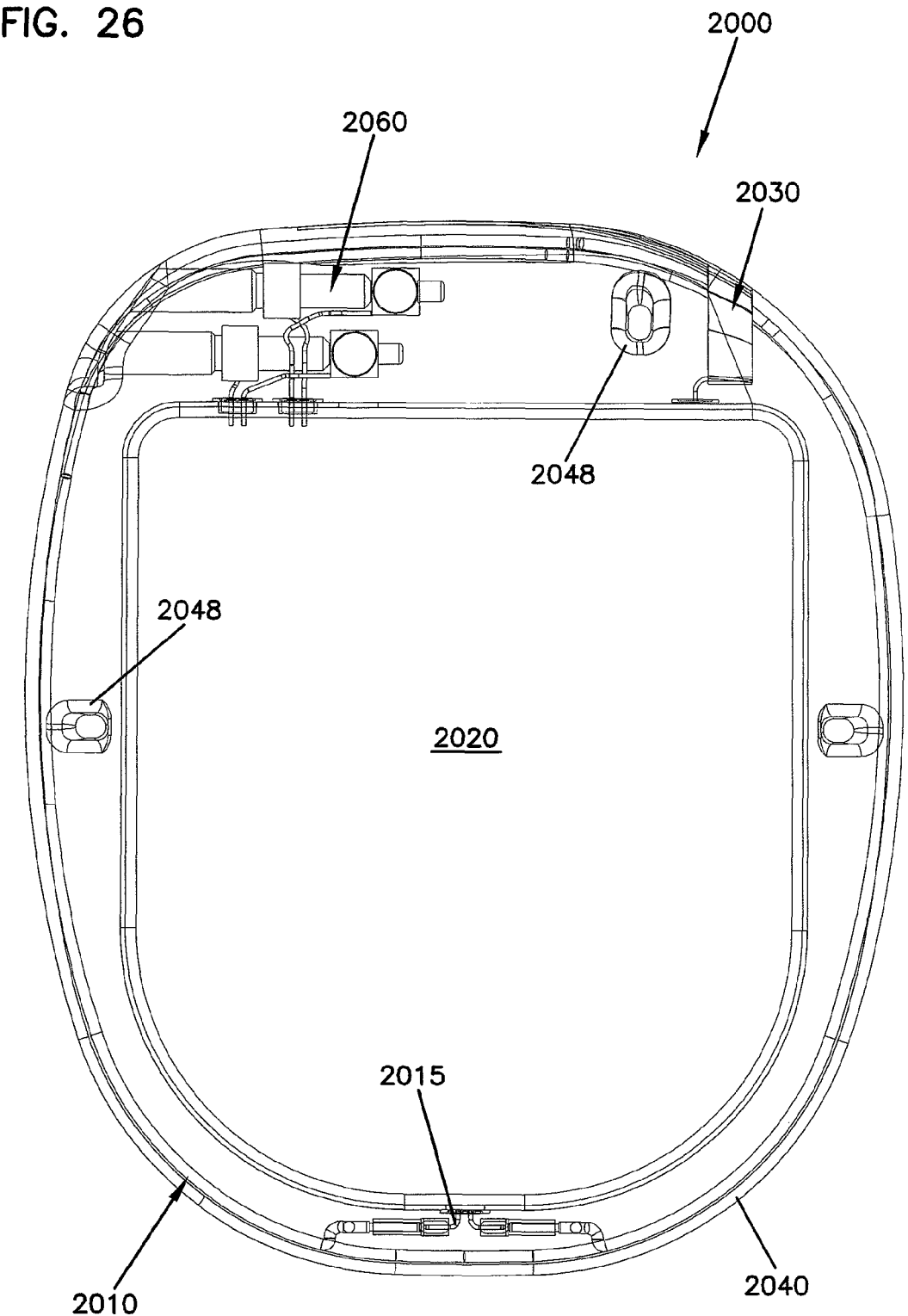
FIG. 26 is a front view of the implantable device of FIG. 25 in accordance with the principles of the present disclosure as described herein.
Figure 27:
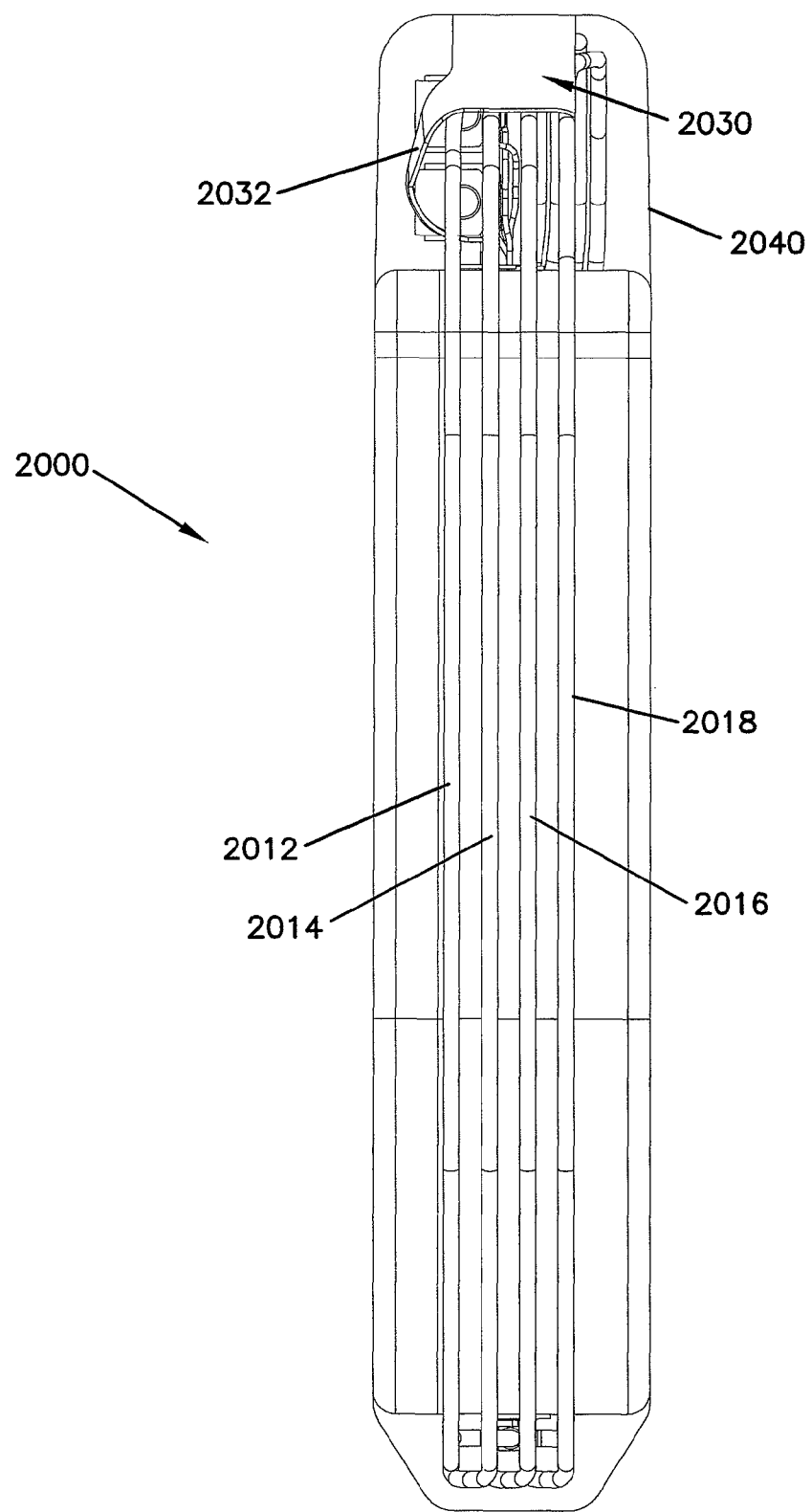
FIG. 27 is a side view of the implantable device of FIG. 25 in accordance with the principles of the present disclosure as described herein.

FIGS. 25-27 illustrate a first example embodiment of an implantable device 2000 including a loop antenna 2010 wrapped around an inner housing 2020 containing components configured to implement telemetry and treatment, such as RF module 110, a treatment module 115, and a rechargeable battery 117 of FIGS. 1 and 2. The loop antenna 2010 couples to the circuitry via antenna port 2015 defined in the inner housing 2020.

In one embodiment, the loop antenna 2010 may be wrapped once around a perimeter of the inner housing 2020. In another embodiment, the loop antenna 2010 may be wrapped about only a portion of the perimeter. In other embodiments, however, the loop antenna 2010 may be wound around the perimeter of the inner housing 2020 multiple times. In the example shown, the loop antenna 2010 is wrapped around the inner housing 2020 about four times (see windings 2012, 2014, 2016, 2018 of FIG. 27).

In one embodiment, the loop antenna 2010 may be wrapped around the inner housing 2020 in a helical pattern (e.g., see FIGS. 25 and 27). In another embodiment, the loop antenna 2010 may be wrapped about the inner housing 2020 in a spiral pattern. Advantageously, a helical winding pattern allows for a smaller circumference than a spiral winding pattern. A spiral winding pattern, however, allows for a thinner form factor than a helical winding pattern.

In another embodiment, the loop antenna 2010 may include sections wound in a spiral shape and other sections wound in a helix shape. For example, in one embodiment, the spiral shaped sections may facilitate routing the loop antenna 2010 around lead sockets of the implantable device 2000 and the helical-shaped sections may be wound around the rest of the implantable device 2000. Accordingly, the antenna configuration for each implantable device may be selected based on the intended implantation site and/or the intended function.

A first unbalanced antenna 2030 may be capacitively coupled to the loop antenna 2010. In the example shown, the first unbalanced antenna 2030 includes an inverted-L antenna. In such an embodiment, the first unbalanced antenna 2030 includes a first section 2032 extending outwardly from the inner housing 2020 and wrapping around the loop antenna 2010. The first unbalanced antenna 2030 also includes a second section 2034 having a generally planar surface extending substantially parallel to the coils of the loop antenna 2010. In other embodiments, the first unbalanced antenna 2030 may include any unbalanced antenna (e.g., a zigzag antenna, a helical antenna, a spiral antenna, a folded antenna, a serpentine antenna, or any other suitable antenna).

In the example shown, the loop antenna 2010 and the unbalanced antenna 2030 are fully enclosed within (i.e., fully insulated by) an outer layer 2040 of a dielectric material. In another embodiment, the outer layer 2040 may enclose only one of these antennae 2010, 2030. In another embodiment, portions of one or both antennae 2010, 2030 may be enclosed within (i.e., partially insulated by) the outer layer 2040. In other embodiments, however, the antennae 2010, 2030 may be exposed (i.e., neither antenna may be enclosed within the outer layer 2040).

Therapy ports 2060 (FIG. 26) for receiving therapy elements, such as therapy elements 170 of FIGS. 1 and 2, also may be defined in the outer layer 2040. In general, the therapy ports 2060 are configured to accept connectors for therapy elements (e.g., lead connectors) in order to form an electrical connection between the therapy elements and components contained in the inner housing 2020 (e.g., the treatment module and a rechargeable battery).

In one embodiment, the outer layer 2040 defines suture passages 2048 by which the implantable device 2000 may be secured in position within the patient. In the example shown in FIGS. 25 and 26, the outer layer 2040 defines three suture passages 2048 extending through the implantable device 2000.

Figure 28:
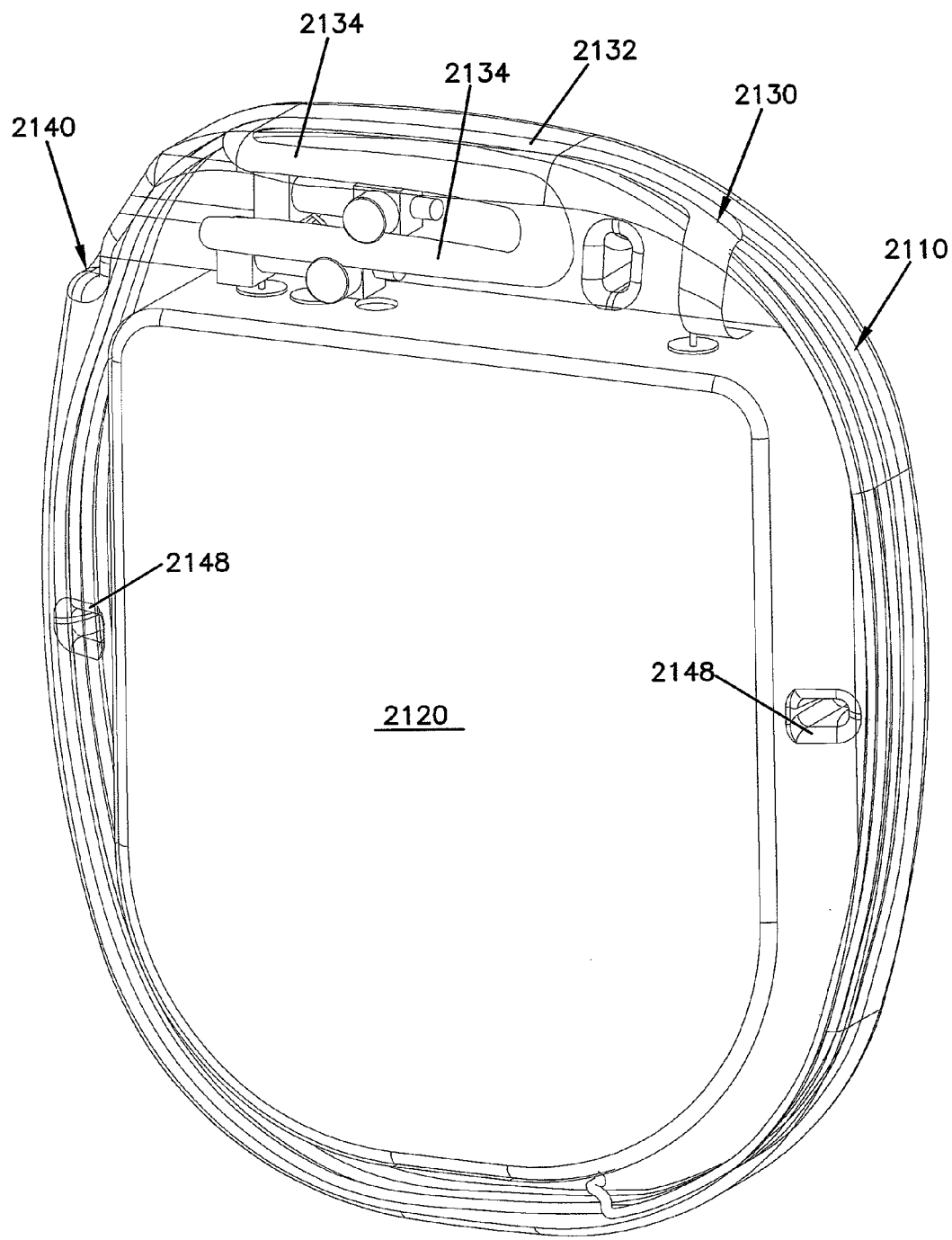
FIG. 28 is a perspective view of another implantable device having a loop antenna wrapped around an inner housing and moderately coupled to a second antenna protruding from the inner housing in accordance with the principles of the present disclosure as described herein.
Figure 29:
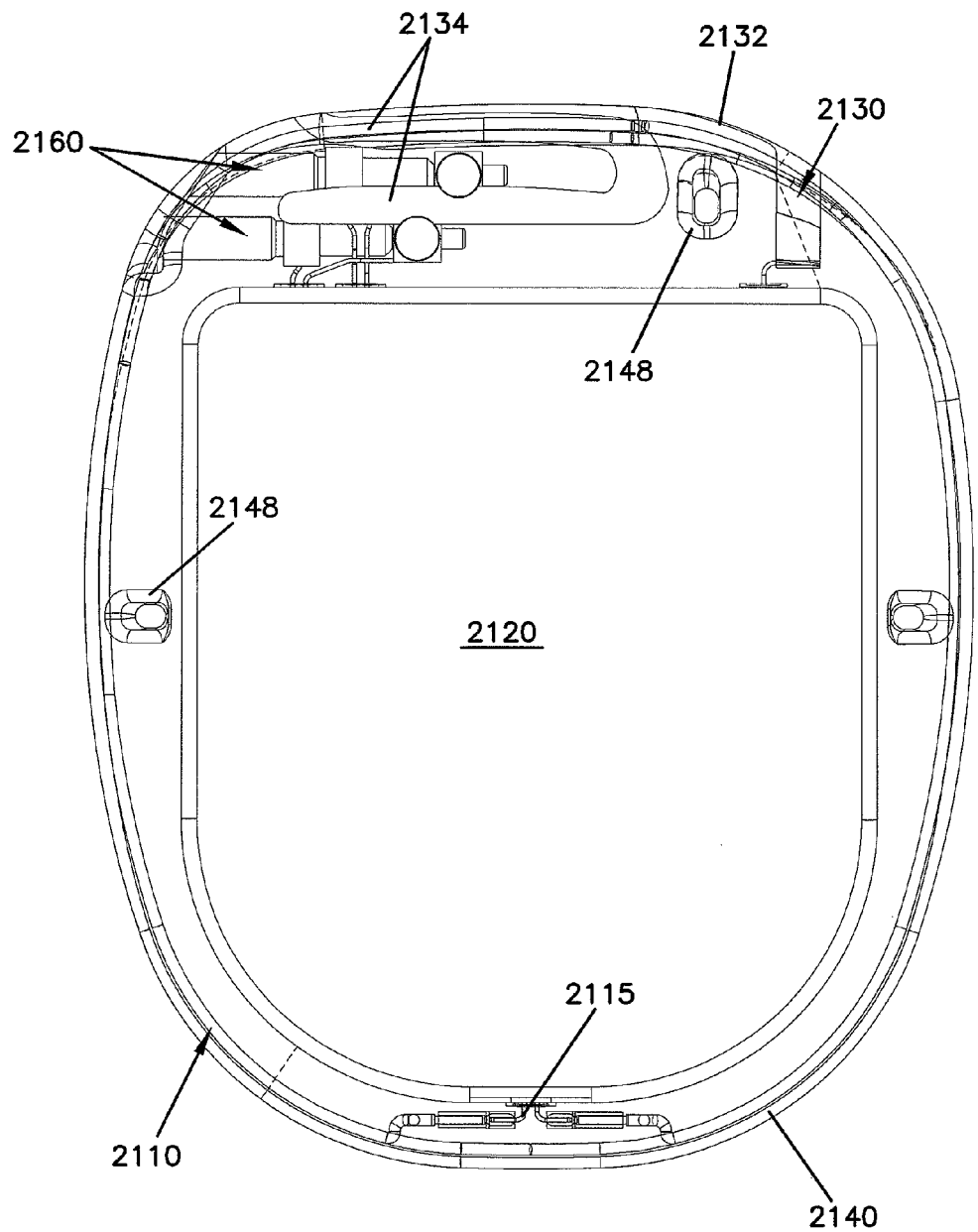
FIG. 29 is a front view of the implantable device of FIG. 28 in accordance with the principles of the present disclosure as described herein.
Figure 30:
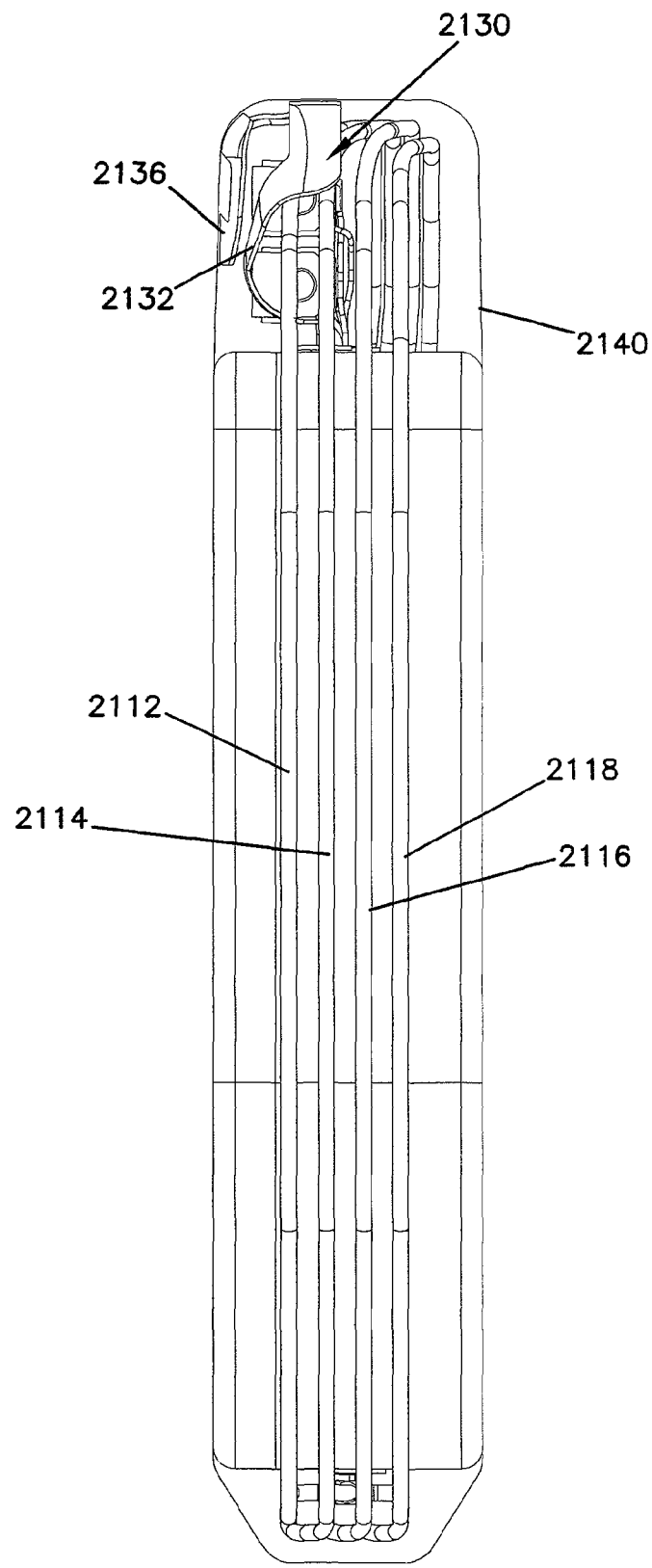
FIG. 30 is a side view of the implantable device of FIG. 28 in accordance with the principles of the present disclosure as described herein.

FIGS. 28-30 illustrate a second example embodiment of an implantable device 2100 including a loop antenna 2110 wrapped around an inner housing 2120 containing treatment components, such as RF module 110, treatment module 115, and rechargeable battery 117 of FIGS. 1 and 2. The loop antenna 2110 couples to the RF module and the treatment module via antenna port 2115 defined in the inner housing 2120. As in the first implantable device 2000, the loop antenna 2110 may be wrapped around a perimeter of the inner housing 2120. In the example shown, the loop antenna 2110 is wrapped around the inner housing 2120 about four times (see windings 2112, 2114, 2116, 2118 of FIG. 29). In other embodiments, however, the loop antenna 2210 may be wrapped fewer or greater times.

A second unbalanced antenna 2130 may be capacitively coupled to the loop antenna 2110. In the example shown, the unbalanced antenna 2130 is another serpentine antenna that is moderately coupled to the loop antenna 2110. In such an embodiment, the second unbalanced antenna 2130 includes a first section 2132 having a planar surface extending substantially parallel and in proximity to the loop antenna 2110 and a second section 2134 having a planar surface extending substantially parallel to, but spaced from the loop antenna 2110.

In the example shown, the loop antenna 2110 and the second unbalanced antenna 2130 are enclosed within (i.e., fully insulated by) an outer layer 2140 of a dielectric material. In another embodiment, the outer layer 2140 may enclose only one of these antennae 2110, 2130. In another embodiment, portions of one or both antennae 2110, 2130 may be enclosed within (i.e., partially insulated by) the outer layer 2140. In other embodiments, however, the antennae 2110, 2130 may be exposed (i.e., neither antenna may be enclosed within the outer layer 2140).

Therapy ports 2160 for receiving therapy elements, such as therapy elements 170 of FIGS. 1 and 2, also may be defined in the outer layer 2140. In general, the therapy ports 2160 are configured to accept connectors for therapy elements (e.g., lead connectors) in order to form an electrical connection between the therapy elements and the components (e.g., the treatment module and a battery) contained in the inner housing 2120. In an embodiment, the outer layer 2140 also defines suture passages 2148 by which the implantable device 2100 may be secured in position within the patient.

Figure 31:
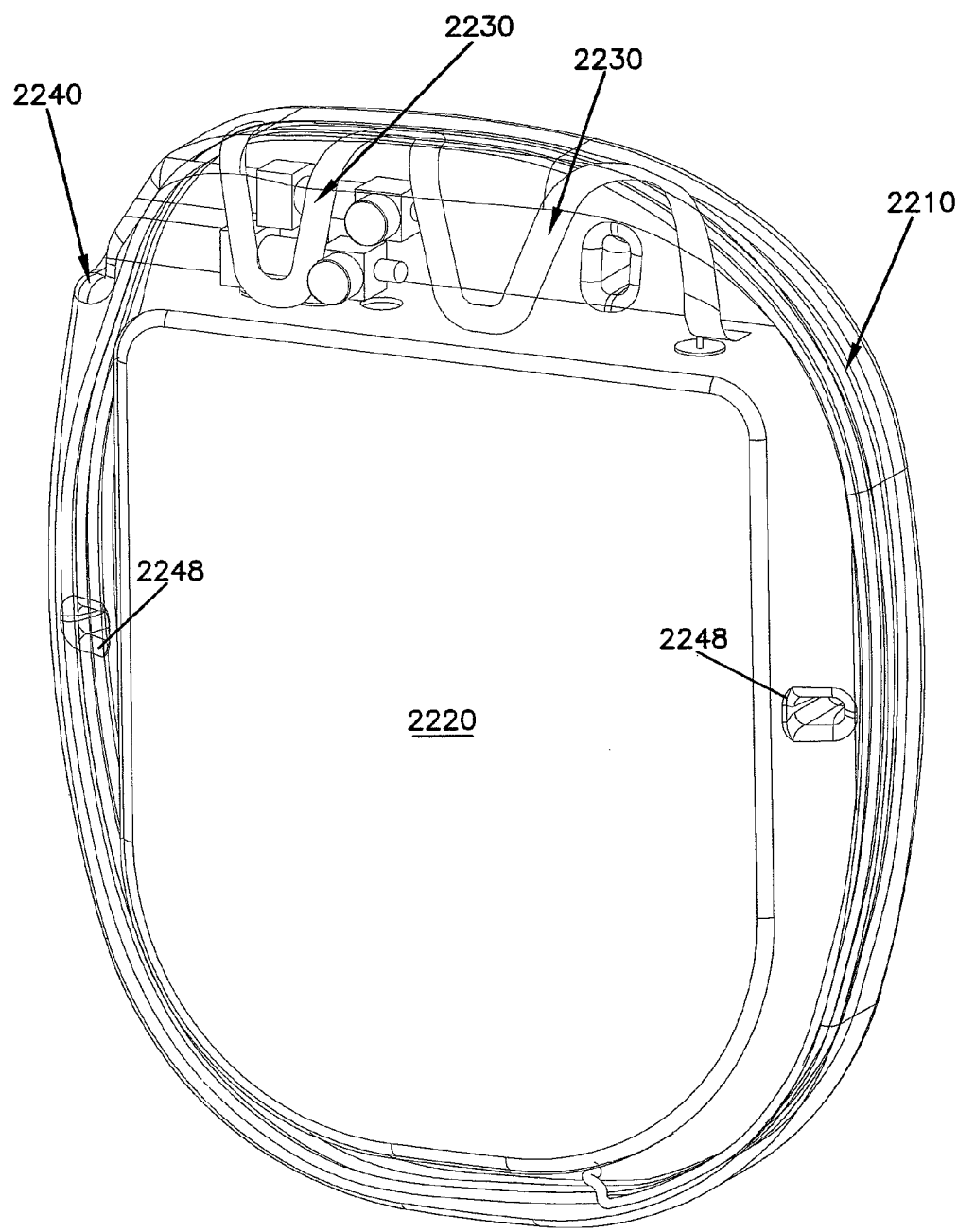
FIG. 31 is a perspective view of an implantable device having a loop antenna wrapped around an inner housing and decoupled from a second antenna protruding from the inner housing in accordance with the principles of the present disclosure as described herein.
Figure 32:
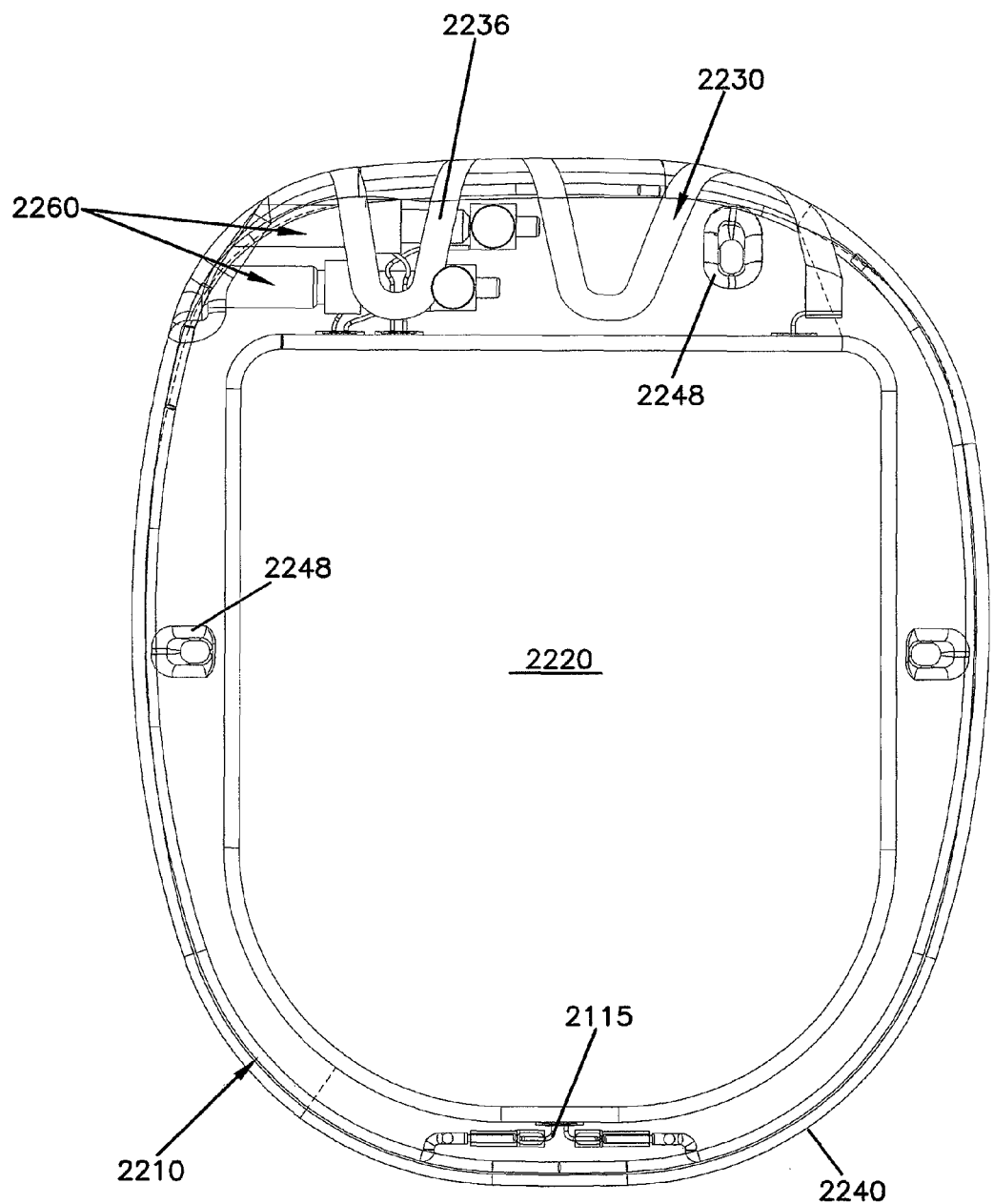
FIG. 32 is a front view of the implantable device of FIG. 31 in accordance with the principles of the present disclosure as described herein.
Figure 33:
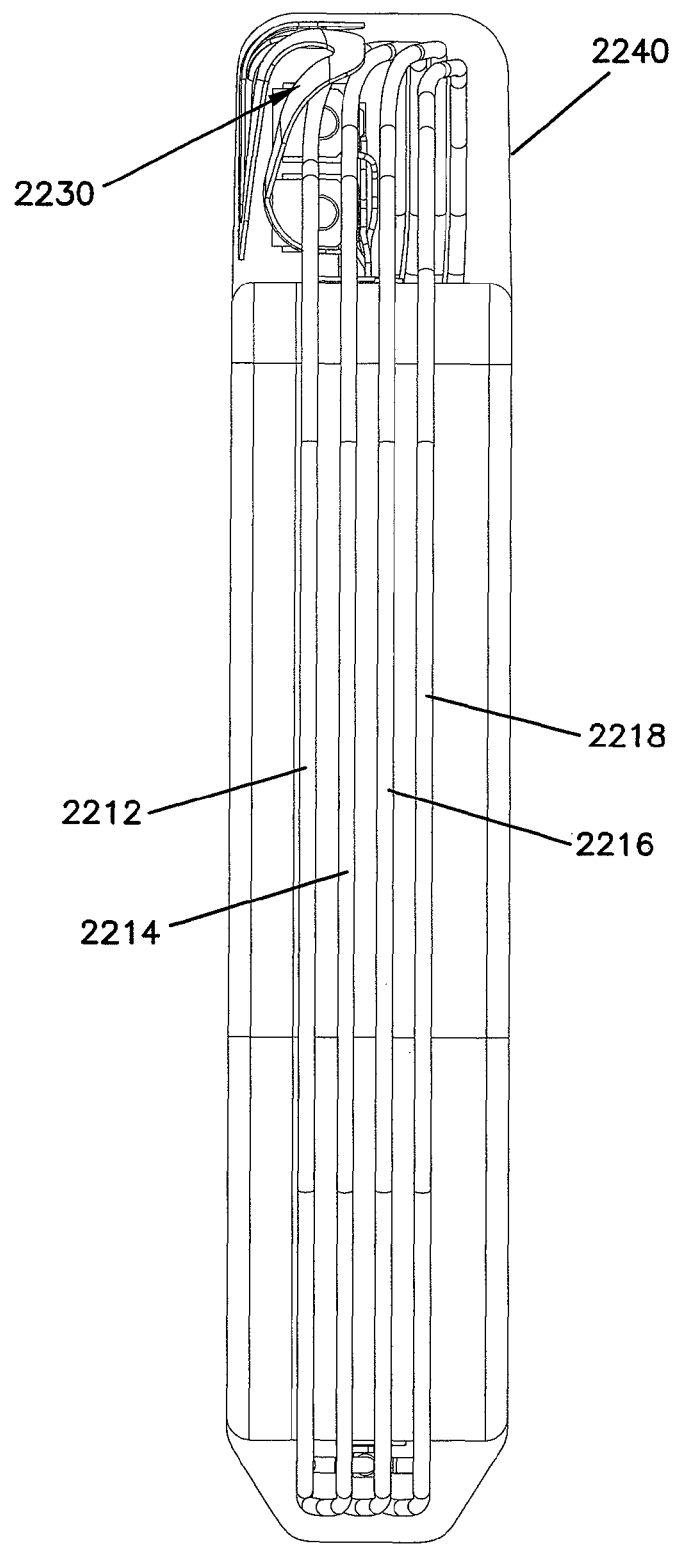
FIG. 33 is a side view of the implantable device of FIG. 31 in accordance with the principles of the present disclosure as described herein.

FIGS. 31-33 illustrate a third example embodiment of an implantable device 2200 including a loop antenna 2210 wrapped around an inner housing 2220 containing an RF module and treatment module, such as RF module 110 and treatment module 115 of FIGS. 1 and 2. The loop antenna 2210 couples to the RF module and the treatment module via antenna port 2215 defined in the inner housing 2220. As in the first implantable device 2000, the loop antenna 2210 may be wrapped around a perimeter of the inner housing 2220. In the example shown, the loop antenna 2210 is wrapped around the inner housing 2220 about four times (see windings 2212, 2214, 2216, 2218 of FIG. 29). In other embodiments, however, the loop antenna 2210 may be wrapped fewer or greater times.

A third unbalanced antenna 2230 may be decoupled from the loop antenna 2210. In the example shown, the unbalanced antenna 2230 is a zigzag antenna that is decoupled from the loop antenna 2210. In such an embodiment, the surface 2236 of the third unbalanced antenna 2230 may extend substantially perpendicular to the coils of the loop antenna 2210.

In the example shown, the loop antenna 2210 and the second unbalanced antenna 2230 are enclosed within (i.e., fully insulated by) an outer layer 2240 of a dielectric material. In another embodiment, the outer layer 2240 may enclose only one of these antennae 2210, 2230. In another embodiment, portions of one or both antennae 2210, 2230 may be enclosed within (i.e., partially insulated by) the outer layer 2240. In other embodiments, however, the antennae 2210, 2230 may be exposed (i.e., neither antenna may be enclosed within the outer layer 2240).

Therapy ports 2260 for receiving therapy elements, such as therapy elements 170 of FIGS. 1 and 2, also may be defined in the outer layer 2240. In general, the therapy ports 2260 are configured to accept connectors for therapy elements (e.g., lead connectors) in order to form an electrical connection between the therapy elements and the components (e.g., the treatment module and a battery) contained in the inner housing 2220. In an embodiment, the outer layer 2240 also defines suture passages 2248 by which the implantable device 2200 may be secured in position within the patient.

The above specification, examples, and data provide a complete description of the manufacture and use of the composition of the invention. Since many embodiments of the invention can be made without departing from the spirit and scope of the invention, the invention resides in the claims hereinafter appended.

We claim:

1. An implantable medical device comprising:
    an inner housing containing a telemetry circuitry and a treatment circuitry, the inner housing defining an antenna port;
    a loop antenna wrapped at least once around an external perimeter of the inner housing and coupled to the telemetry circuitry through the antenna port;
    a first unbalanced antenna capacitively coupled to the loop antenna; and
    an outer layer of a dielectric material surrounding at least a portion of the first unbalanced antenna, the outer layer defining therapy ports configured to provide an electrical connection to the treatment circuitry of the inner housing;
    wherein the implantable medical device is configured for implantation within a body of a patient.

2. The implantable medical device of claim 1, wherein the loop antenna is wound around the external perimeter of the inner housing multiple times.

3. The implantable medical device of claim 2, wherein the loop antenna is wrapped around the external perimeter of the inner housing about four times.

4. The implantable medical device of claim 1, wherein the loop antenna is wrapped around the external perimeter of the inner housing in a helical pattern.

5. The implantable medical device of claim 1, wherein the loop antenna is wrapped around the external perimeter of the inner housing in a spiral pattern.

6. The implantable medical device of claim 1, wherein a first section of the loop antenna is wrapped around the external perimeter of the inner housing in a spiral pattern and a second section of the loop antenna is wrapped around the external perimeter of the inner housing in a helical pattern.

7. The implantable medical device of claim 1, wherein the first unbalanced antenna includes a first section extending outwardly from the inner housing and wrapping around the loop antenna and a second section having a generally planar surface extending substantially parallel to windings of the loop antenna.

8. The implantable medical device of claim 1, wherein the first unbalanced antenna includes a zigzag antenna.

9. The implantable medical device of claim 1, wherein the first unbalanced antenna includes a helical antenna.

10. The implantable medical device of claim 1, wherein the first unbalanced antenna includes a folded antenna.

11. The implantable medical device of claim 1, wherein the first unbalanced antenna includes a serpentine antenna.

12. The implantable medical device of claim 11, wherein the first unbalanced antenna includes a first section having a planar surface extending substantially parallel and in proximity to the loop antenna and a second section having a planar surface extending substantially parallel to, but spaced from the loop antenna.

13. The implantable medical device of claim 1, wherein the outer layer fully surrounds the first unbalanced antenna.

14. The implantable medical device of claim 1, wherein the outer layer fully surrounds the loop antenna and the first unbalanced antenna.

15. The implantable medical device of claim 1, wherein the inner housing contains at least one switching circuit configured to receive current induced on the loop antenna when a signal is received, the switching circuit is configured to determine a type of signal received and to provide power to an appropriate one of the circuits contained within the inner housing based on the type of signal received.

16. The implantable medical device of claim 15, wherein the switching circuitry determines which of the circuits contained within the inner housing is the appropriate circuit based on a frequency of the signals received at the loop antenna.

17. An implantable medical device comprising:
    an inner housing containing a telemetry circuitry and a treatment circuitry, the inner housing defining an antenna port;
    a loop antenna wrapped in a plurality of coils around an external perimeter of the inner housing and coupled to the telemetry circuitry through the antenna port;
    a first unbalanced antenna decoupled from the loop antenna; and
    an outer layer of a dielectric material surrounding at least a portion of the first unbalanced antenna, the outer layer defining therapy ports configured to provide an electrical connection to the treatment circuitry of the inner housing;
    wherein the implantable medical device is configured for implantation within a body of a patient.

18. The implantable medical device of claim 17, wherein the first unbalanced antenna includes a zigzag antenna.

19. The implantable medical device of claim 18, wherein the first unbalanced antenna includes a surface that extends substantially perpendicular to the coils of the loop antenna.

20. The implantable medical device of claim 17, wherein the outer layer fully surrounds the loop antenna and the first unbalanced antenna.

* * * * *